US010905742B2

(12) United States Patent
Kosai et al.

(10) Patent No.: US 10,905,742 B2
(45) Date of Patent: Feb. 2, 2021

(54) APPLICATION OF HEPARIN-BINDING EPIDERMAL GROWTH FACTOR-LIKE GROWTH FACTOR FOR MEDICAL PURPOSES

(75) Inventors: Ken-ichiro Kosai, Kagoshima (JP); Cin Khai Ngin, Kagoshima (JP); Tomoyuki Takahashi, Kurume (JP)

(73) Assignee: KAGOSHIMA UNIVERSITY, Kagoshima (JP)

( * ) Notice: Subject to any disclaimer, the term of this patent is extended or adjusted under 35 U.S.C. 154(b) by 516 days.

(21) Appl. No.: 11/992,728

(22) PCT Filed: Sep. 28, 2006

(86) PCT No.: PCT/JP2006/319915
§ 371 (c)(1),
(2), (4) Date: May 15, 2008

(87) PCT Pub. No.: WO2007/037514
PCT Pub. Date: Apr. 5, 2007

(65) Prior Publication Data
US 2009/0130062 A1 May 21, 2009

(30) Foreign Application Priority Data
Sep. 28, 2005 (JP) ................... 2005-283085

(51) Int. Cl.
*C12N 15/86* (2006.01)
*A61K 38/18* (2006.01)
*A61K 48/00* (2006.01)

(52) U.S. Cl.
CPC ........ *A61K 38/1808* (2013.01); *A61K 48/005* (2013.01); *C12N 15/86* (2013.01); *C12N 2710/10332* (2013.01); *C12N 2710/10343* (2013.01); *C12N 2710/10371* (2013.01)

(58) Field of Classification Search
CPC .................. A61K 38/1808; A61K 48/005
See application file for complete search history.

(56) References Cited

FOREIGN PATENT DOCUMENTS

WO    98/24467    6/1998
WO    99/54706    10/1999

OTHER PUBLICATIONS

Pahlavan et al (Journal of Surgical Research 134, 238-251, 2006).*
(Gonin et al, (Gene Therapy, 11: 598-5108, 2004).*
Guicciardi et al (Digest Liver Dis, 34: 387-92, 2002).*
Bouard et al. (Br J Pharmacol, 157(2): 153-65, 2009).*
Sakamoto et al (International Journal of Molecular Medicine, 38: 1673-1682, 2016) (Year: 2016).*
Phaneuf et al, (Molecular Medicine, 6(2): 96-103, 2000) (Year: 2000).*
Michalopoulos et al (Adv Biochem Engin/Biotechnol, 93: 101-134, 2005) (Year: 2005).*
K. Kosai et al., "Retrovirus-Mediated In Vivo Gene Transfer in the Replicating Liver Using Recombinant Hepatocyte Growth Factor Without Liver Injury or Partial Hepatectomy", Human Gene Therapy, vol. 9, pp. 1293-1301, Jun. 10, 1998.
K. Kosai et al., "Abrogation of Fas-Induced Fulminant Hepatic Failure in Mice by Hepatocyte Growth Factor", Biochemical and Biophysical Research Communication, vol. 244, pp. 683-690, 1998.
K. Kosai et al., "Hepatocyte Growth Factor Prevents Endotoxin-Induced Lethal Hepatic Failure in Mice", Hepatology, vol. 30, No. 1, pp. 151-159, Jul. 1999.
J. Kozawa et al., "Regenerative and Therapeutic Effects of Heparin-Binding Epidermal Growth Factor-Like Growth Factor on Diabetes by Gene Transduction Through Retrograde Pancreatic Duct Injection of Adenovirus Vector", Pancreas, vol. 31, No. 1, pp. 32-42, Jul. 2005.
H. Ushikoshi et al., "Local Overexpression of HB-EGF Exacerbates Remodeling Following Myocardial Infarction by Activating Noncardiomyocytes", Laboratory Investigation, vol. 85, pp. 862-873, 2005.
C. Mitchell et al., "Heparin-Binding Epidermal Growth Factor-Like Growth Factor Links Hepatocyte Priming with Cell Cycle Progression During Liver Regeneration", The Journal of Biological Chemistry, vol. 280, No. 4, pp. 2562-2568, Jan. 28, 2005.
S. Kiso et al., "Liver Regeneration in Heparin-Binding EGF-Like Growth Factor Transgenic Mice after Partial Hepatectomy", Gastroenterology, vol. 124, pp. 701-707, 2003.
S. Kiso et al., "Effects of Exogenous Human Heparin-Binding Epidermal Growth Factor-Like Growth Factor on DNA Synthesis of Hepatocytes in Normal Mouse Liver", Biochemical and Biophysical Research Communications, vol. 259, pp. 683-687, 1999.
S. Kiso et al., "Expression of Heparin-Binding EGF-Like Growth Factor in Rat Liver Injured by Carbon Tetrachloride of D-Galactosamine", Biochemical and Biophysical Research Communications, vol. 220, pp. 285-288, 1996.
N. Hayashi et al., J. Japanese Society of Internal Medicine, vol. 86, pp. 88-91, 1997.
S. Kawata et al., Rinsho Kagaku, vol. 34, pp. 1229-1235, 1998.
Supplementary European Search Report dated Nov. 2, 2009 in corresponding European Application No. 06811253.
N. Ito et al., "Heparin-Binding EGF-Like Growth Factor Is a Potent Mitogen for Rat Hepatocytes", Biochemical and Biophysical Research Communications, vol. 198, No. 1, pp. 25-31, Jan. 14, 1994.

(Continued)

*Primary Examiner* — Ram R Shukla
*Assistant Examiner* — Magdalene K Sgagias
(74) *Attorney, Agent, or Firm* — Wenderoth, Lind & Ponack, L.L.P.

(57) ABSTRACT

The present invention provides an agent for protecting the liver and/or promoting liver regeneration, which contains a heparin-binding EGF-like growth factor-like growth factor (HB-EGF) or a partial peptide thereof, or a nucleic acid that encodes same, and an agent for the prophylaxis or treatment of liver diseases. The present invention further provides a method for producing a cell for liver protection and/or promoting liver regeneration, and for the prophylaxis/treatment of a liver disease, which includes introducing a nucleic acid that encodes HB-EGF or a partial peptide thereof into a cell collected from an animal.

10 Claims, 5 Drawing Sheets

Specification includes a Sequence Listing.

(56) References Cited

OTHER PUBLICATIONS

A. Moriuchi et al., "Additive and Inhibitory Effects of Simultaneous Treatment with Growth Factors on DNA Synthesis through MAPK Pathway and G1 Cyclins in Rat Hepatocytes", Biochemical and Biophysical Research Communications, vol. 280, pp. 368-373, Jan. 12, 2001.

N. Khai et al., "HB-EGF Gene Therapy is More Potently Therapeutic (Protective and Mitogenic for Hepatocytes) Than HGF for Hepatic Injury in Mice", Journal of Gene Medicine, vol. 8, pp. 1465-1466 (2006); and Abstracts from the 12th Annual Meeting of the Japan Society of Gene Therapy, Tokyo Japan, Aug. 24-26, 2006.

N. Khai et al., "In vivo hepatic HB-EGF gene transduction inhibits Fas-induced liver injury and induces liver regeneration in mice: A comparative study to HGF", Journal of Hepatology, vol. 44, No. 6, pp. 1046-1054, Jun. 1, 2006.

Japanese Office Action dated May 17, 2011 in Japanese Patent Application No. 2007-537770 (with Partial Translation).

E. Miyoshi et al., "Membrane-anchored Heparin-binding Epidermal Growth Factor-like Growth Factor Acts as a Tumor Survival Factor in a Hepatoma Cell Line," *The Journal of Biological Chemistry*, vol. 272, No. 22, pp. 14349-14355 (1997).

\* cited by examiner

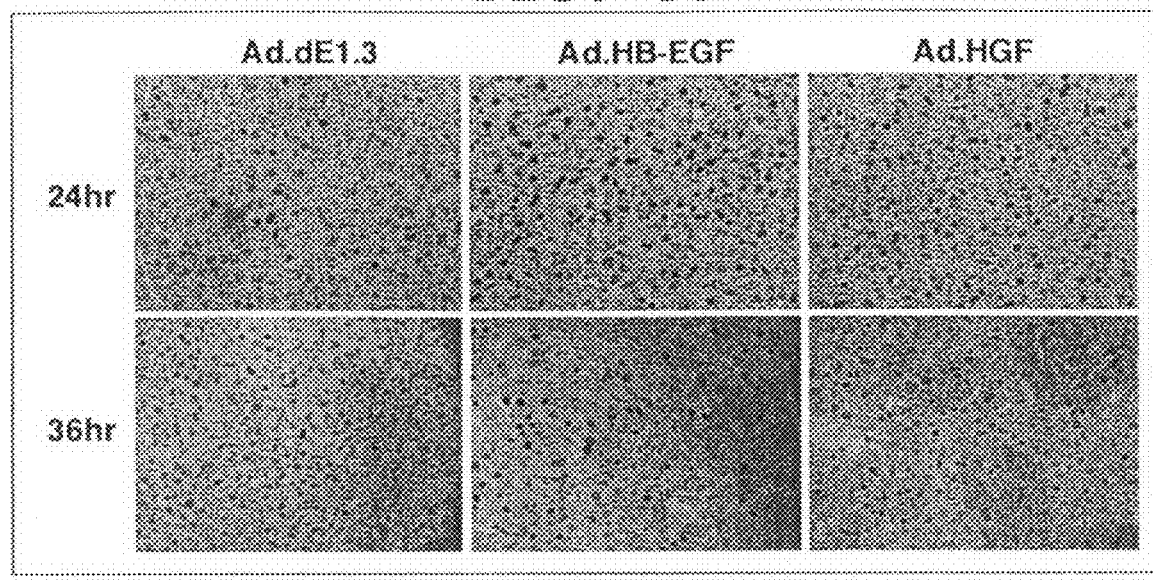
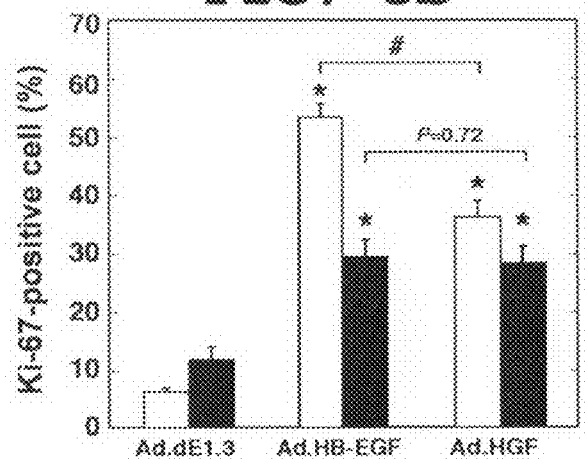

SEQUENCE LISTING

<160> NUMBER OF SEQ ID NOS: 2

<210> SEQ ID NO 1
<211> LENGTH: 624
<212> TYPE: DNA
<213> ORGANISM: Homo sapiens
<220> FEATURE:
<221> NAME/KEY: CDS
<222> LOCATION: (1)..(624)

<400> SEQUENCE: 1

```
atg aag ctg ctg ccg tcg gtg gtg ctg aag ctc ttt ctg gct gca gtt        48
Met Lys Leu Leu Pro Ser Val Val Leu Lys Leu Phe Leu Ala Ala Val
1               5                   10                  15 ctc tcg gca ctg gtg act ggc gag agc ctg gag cgg ctt cgg aga ggg        96
Leu Ser Ala Leu Val Thr Gly Glu Ser Leu Glu Arg Leu Arg Arg Gly
                20                  25                  30 cta gct gct gga acc agc aac ccg gac cct ccc act gta tcc acg gac       144
Leu Ala Ala Gly Thr Ser Asn Pro Asp Pro Pro Thr Val Ser Thr Asp
            35                  40                  45 cag ctg cta ccc cta gga ggc ggc cgg gac cgg aaa gtc cgt gac ttg       192
Gln Leu Leu Pro Leu Gly Gly Gly Arg Asp Arg Lys Val Arg Asp Leu
        50                  55                  60 caa gag gca gat ctg gac ctt ttg aga gtc act tta tcc tcc aag cca       240
Gln Glu Ala Asp Leu Asp Leu Leu Arg Val Thr Leu Ser Ser Lys Pro
65                  70                  75                  80 caa gca ctg gcc aca cca aac aag gag gag cac ggg aaa aga aag aag       288
Gln Ala Leu Ala Thr Pro Asn Lys Glu Glu His Gly Lys Arg Lys Lys
                85                  90                  95 aaa ggc aag ggg cta ggg aag aag agg gac cca tgt ctt cgg aaa tac       336
Lys Gly Lys Gly Leu Gly Lys Lys Arg Asp Pro Cys Leu Arg Lys Tyr
                100                 105                 110 aag gac ttc tgc atc cat gga gaa tgc aaa tat gtg aag gag ctc cgg       384
Lys Asp Phe Cys Ile His Gly Glu Cys Lys Tyr Val Lys Glu Leu Arg
            115                 120                 125 gct ccc tcc tgc atc tgc cac ccg ggt tac cat gga gag agg tgt cat       432
Ala Pro Ser Cys Ile Cys His Pro Gly Tyr His Gly Glu Arg Cys His
        130                 135                 140 ggg ctg agc ctc cca gtg gaa aat cgc tta tat acc tat gac cac aca       480
Gly Leu Ser Leu Pro Val Glu Asn Arg Leu Tyr Thr Tyr Asp His Thr
145                 150                 155                 160 acc atc ctg gcc gtg gtg gct gtg gtg ctg tca tct gtc tgt ctg           528
```

```
Thr Ile Leu Ala Val Val Ala Val Val Leu Ser Ser Val Cys Leu Leu
            165                 170                 175 gtc atc gtg ggg ctt ctc atg ttt agg tac cat agg aga gga ggt tat      576
Val Ile Val Gly Leu Leu Met Phe Arg Tyr His Arg Arg Gly Gly Tyr
            180                 185                 190 gat gtg gaa aat gaa gag aaa gtg aag ttg ggc atg act aat tcc cac      624
Asp Val Glu Asn Glu Glu Lys Val Lys Leu Gly Met Thr Asn Ser His
            195                 200                 205

<210> SEQ ID NO 2
<211> LENGTH: 208
<212> TYPE: PRT
<213> ORGANISM: Homo sapiens

<400> SEQUENCE: 2

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Thr Val Ser Thr Asp
        35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
            115                 120                 125

Ala Pro Ser Cys Ile Cys His Pro Gly Tyr His Gly Glu Arg Cys His
        130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
            165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
            195                 200                 205
```

APPLICATION OF HEPARIN-BINDING EPIDERMAL GROWTH FACTOR-LIKE GROWTH FACTOR FOR MEDICAL PURPOSES

This application is a U.S. national stage of International Application No. PCT/JP2006/319915 filed Sep. 28, 2006.

TECHNICAL FIELD

The present invention relates to a novel pharmaceutical use of a heparin-binding EGF-like growth factor (hereinafter to be abbreviated as "HB-EGF") or a nucleic acid encoding the same, and more specifically, use for the prophylaxis/treatment of a liver disease.

BACKGROUND ART

Pharmaceutical agents and treatment methods for liver diseases currently used in clinical situations merely aim at symptomatic therapy, and there is no definitive agent or definitive therapy that inhibits liver damage (hepatocyte death) and induces liver regeneration. At present, therefore, the primary course of treatment for acute hepatitis is rest and diet. In fact, none of the pharmaceutical agents currently in use has demonstrated true effectiveness for the disease. In particular, although various pharmaceutical agents and treatment methods have been employed for fulminant hepatic failure, the death rate from the disease is still close to 70%, proving that they are far from effective pharmaceutical agents and treatment methods. In Europe and the United States, liver transplantation is the first choice of treatment.

As stated above, in the actual situation, a definitive drug for liver diseases (particularly fulminant hepatic failure) does not exist at the clinical level. Under the circumstances, hepatocyte growth factor (HGF) has been confirmed effective at the research level, and is expected most for practical application soon. One of the present inventors previously reported that HGF strongly inhibits hepatocyte death and simultaneously induces liver regeneration after liver damage in a fulminant hepatic failure model (WO 98/24467; Kosai, K. et al., *Hum. Gene Ther.,* 9: 1293-1301 (1998); Kosai, K. et al., *Biochem. Biophys. Res. Commun.,* 244: 683-90 (1998); Kosai, K. et al., *Hepatology,* 30: 151-9 (1999)), and the development is ongoing for the clinical application.

HB-EGF is a growth factor belonging to the EGF family, which is also expressed in normal liver. It has biologically unique characteristics in that it is first synthesized as a membrane-binding type precursor (proHB-EGF), cleaved by a specific metalloproteinase at the juxtamembrane domain, and the resulting soluble HB-EGF shows a mitogenic action on many types of cells. In the liver, HB-EGF shows a sharp increase in expression after hemihepatectomy, and also shows promoted expression in chronic liver diseases. Based on these facts, HB-EGF has been, like HGF and the like, presumed to be one of the hepatotrophic factors.

Moreover, it has been reported that the administration of and gene therapy with HB-EGF show a therapeutic effect on some of the organ disorders. For example, it has been suggested that administration of recombinant HB-EGF (including topical production by gene therapy) to damaged epithelial cells of patients with interstitial cystitis (IC) can block the effect of an antiproliferative factor (APF) causing epithelial abnormality in IC, and alleviate or remove chronic damage in the bladder epithelium (WO 99/54706). Furthermore, an backward injection of an adenoviral vector containing HB-EGF gene to a diabetic mouse from the pancreatic duct affords growth of pancreatic β cells, differentiation of pancreatic duct cells into insulin-producing cells and improvement in glucose tolerance, suggesting that HB-EGF shows a pancreas regeneration and diabetes treating effect (Kozawa, J. et al., *Pancreas,* 31: 32-42 (2005)).

However, no report has so far documented that HB-EGF actually shows a therapeutic effect on liver diseases, namely, exogenous HB-EGF suppresses liver damage and/or induces liver regeneration. Moreover, although HB-EGF is, like HGF and insulin-like growth factor (IGF), known as a cardiohypertrophic growth factor, a gene therapy using HB-EGF did not show any therapeutic effect unlike use of HGF or IGF, in a myocardial infarction treatment test using rabbit conducted by the present inventors. Conversely, it rather aggravated remodeling after infarction (Ushikoshi, H. et al., *Lab. Invest.,* 85: 862-73 (2005)). Thus, it seems that HB-EGF does not necessarily act therapeutically on all organ disorders.

As described above, it is completely unknown whether or not HB-EGF actually shows a therapeutic effect on liver diseases, not to mention the effectiveness of its gene therapy which provides no guarantee at all.

DISCLOSURE OF THE INVENTION

It is therefore an object of the present invention to provide a novel and more useful prophylactic or therapeutic drug for a liver disease (particularly fulminant hepatic failure) by identifying a substance that shows a stronger liver damage suppressing and liver regeneration inducing action than HGF does.

The present inventors have introduced and expressed an adenoviral vector containing a DNA encoding HB-EGF in an animal fulminant hepatic failure model and found that HB-EGF remarkably suppresses liver damage and hepatocyte apoptosis and induces liver regeneration. More surprisingly, the treatment effects of HB-EGF have been found to be stronger than those of HGF, the currently-known most promising therapeutic drug for liver diseases. The inventors have conducted further investigations based on these findings, and completed the present invention.

Accordingly, the present invention provides an agent for protecting the liver and/or promoting liver regeneration, which comprises a nucleic acid encoding HB-EGF or a partial peptide thereof. When the nucleic acid is introduced into target cells by way of, for example, a viral vector described below or the like, into which the nucleic acid has been inserted, it is intracellularly expressed to produce and release HB-EGF or a partial peptide thereof, and suppresses liver damage (hepatocyte death) as well as induces liver regeneration.

Therefore, the present invention also provides an agent for protecting the liver and/or promoting liver regeneration, which comprises HB-EGF or a partial peptide thereof. The protein (or peptide) can be produced in large amounts using the gene recombination technique as described below, and used.

Furthermore, the present invention provides a method of producing cells for protecting the liver and/or promoting liver regeneration, which comprises introducing a nucleic acid encoding HB-EGF or a partial peptide thereof into cells collected from an animal. By putting back the cells collected from an individual, into which the nucleic acid has been introduced and whose expression has been confirmed, to the individual or implanting the cells into a different individual, liver damage (hepatocyte death) is suppressed and liver regeneration is induced in the animal individual.

Since HB-EGF shows a strong liver damage suppressive, apoptosis suppressive and liver regeneration inducing action, it provides a prophylactic or therapeutic effect on various diseases accompanying liver damage or hepatocyte death by administration of HB-EGF or a nucleic acid encoding HB-EGF.

Specific embodiments of the present invention and other advantages and the like of the present invention are described in more detail in "Best Mode for Embodiment of the Invention" below.

BRIEF DESCRIPTION OF THE DRAWINGS

FIG. 1 shows that the target gene can be efficiently introduced into the liver and hepatocyte by injection of an adenoviral vector from the tail vein.

FIG. 2 shows an influence of the administration of Ad.HB-EGF, Ad.HGF or Ad.dE1.3 on the blood concentration of liver enzyme of fulminant hepatic failure model mice.

FIG. 4 shows the results of TUNEL staining of the livers of fulminant hepatic failure model mice administered with Ad.HB-EGF, Ad.HGF or Ad.dE1.3.

FIG. 5 shows an influence of the administration of Ad.HB-EGF, Ad.HGF or Ad.dE1.3 on liver regeneration in fulminant hepatic failure model mice. FIG. 5A shows, from the left, Ki-67-stained images of the livers of the Ad.dE1.3-, Ad.HB-EGF- or Ad.HGF-administration group mice (top: 24 hr after antibody administration, bottom: 36 hr after antibody administration). FIG. 5B is a graph showing quantified Ki-67-positive cells (white bar: 24 hr after antibody administration, black bar: 36 hr after antibody administration).

BEST MODE FOR EMBODIMENT OF THE INVENTION

Figure 1A:
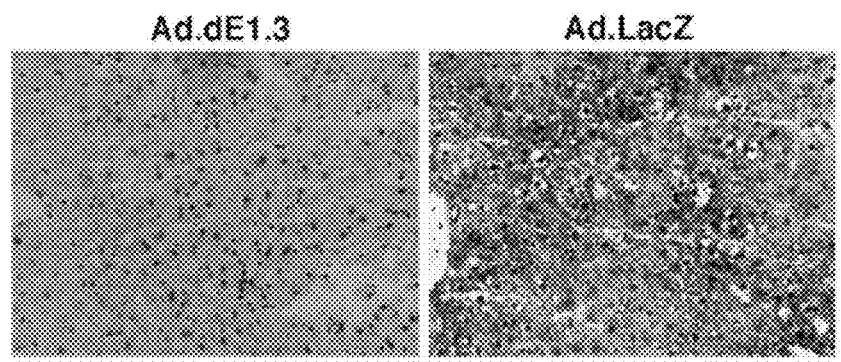
FIG. 1A shows that X-gal staining positive cells are observed throughout the liver tissues after Ad.LacZ introduction.

With regard to HB-EGF used for the present invention, derivation thereof is not particularly limited, as long as it is a protein containing the same or substantially the same amino acid sequence as an amino acid sequence shown by SEQ ID NO:2, and it can be a protein derived from a cell [for example, hepatocyte, splenocyte, nerve cell, glial cell, pancreatic β cell, bone marrow cell, mesangial cell, Langerhans cell, epidermal cell, epithelial cell, goblet cell, endothelial cell, smooth muscle cell, skeletal muscle cell, fibroblast, fiber cell, adipocyte, immune cell (e.g., macrophage, T cell, B cell, natural killer cell, mast cell, neutrophil, basophil, eosinophil, monocyte), megakaryocyte, synovial cell, chondrocyte, osteocyte, osteoblast, osteoclast, mammary cell or interstitial cell, or precursor cell, stem cell, established or cancer cell thereof, and the like] of human or other warm-blooded animal (e.g., bovine, swine, mouse, rat, hamster, monkey, horse, sheep, goat, rabbit, guinea pig, chicken and the like) or any tissue or organ in which these cells are present [for example, brain, any portion of brain (e.g., olfactory bulb, amygdaloid nucleus, basal ganglia, hippocampus, thalamus, hypothalamus, cerebral cortex, medulla oblongata, cerebellum), spinal cord, pituitary gland, stomach, pancreas, kidney, liver, gonad, thyroid gland, gall bladder, bone marrow, adrenal gland, skin, muscle (skeletal muscle, smooth muscle), lung, gastrointestinal tract (e.g., large intestine, small intestine), blood vessel, heart, thymus, spleen, submandibular gland, peripheral blood, urinary duct, prostate, orchis, ovary, placenta, uterus, bone, joint, adipose tissue (e.g., brown adipose tissue, white adipose tissue) and the like], or may be a synthetic protein synthesized chemically or biochemically using a cell-free protein synthesis system as described below. Alternatively, this protein may be a recombinant protein produced from a transformant introduced with a nucleotide having the base sequence encoding the above-described amino acid sequence.

Substantially the same amino acid sequence as the amino acid sequence shown by SEQ ID NO:2 refers to an amino acid sequence having a homology of about 70% or more, preferably about 80% or more, more preferably about 90% or more, and particularly preferably about 95% or more, to the amino acid sequence shown by SEQ ID NO:2, wherein the proteins containing the amino acid sequence have substantially the identical activity to the protein containing the amino acid sequence shown by SEQ ID NO:2. "Homology" herein means a proportion (%) of the same amino acid residue and analogous amino acid residue to the whole amino acid residues overlapped in the optimal alignment (preferably, the algorithm is such that a gap can be introduced into one or both of the sequences for an optimal alignment) where two amino acid sequences are aligned using a mathematic algorithm known in the technical field. The "analogous amino acid" means amino acids having similar physiochemical properties, and, for example, the amino acids are classified into groups such as an aromatic amino acid (Phe, Trp, Tyr), an aliphatic amino acid (Ala, Leu, Ile, Val), a polar amino acid (Gln, Asn), a basic amino acid (Lys, Arg, H is), an acidic amino acid (Glu, Asp), an amino acid having a hydroxy group (Ser, Thr) and an amino acid having a small side-chain (Gly, Ala, Ser, Thr, Met). Substitution by such analogous amino acids is expected not to change the phenotype of proteins (i.e., conservative amino acid substitution). Specific examples of the conservative amino acid substitution are known in this technical field and described in various literatures (e.g., see Bowie et al., Science, 247: 1306-1310 (1990)).

The homology of the amino acid sequence in the present specification can be calculated using homology calculation algorithm NCBI BLAST (National Center for Biotechnology Information Basic Local Alignment Search Tool) under the following conditions (expectancy=10; allowing gap; matrix=BLOSUM62; filtering=OFF). Other algorithms to determine a homology of amino acid sequence include, for example, the algorithm as described in Karlin et al., Proc. Natl. Acad. Sci. USA, 90: 5873-5877 (1993) [the algorithm is incorporated into NBLAST and XBLAST programs (version 2.0) (Altschul et al., Nucleic Acids Res., 25: 3389-3402

(1997))], the algorithm as described in Needleman et al., J. Mol. Biol., 48: 444-453 (1970) [the algorithm is incorporated into a GAP program in a GCG software package], the algorithm as described in Myers and Miller, CABIOS, 4: 11-17 (1988) [the algorithm is incorporated into an ALIGN program (version 2.0) which is a part of a CGC sequence alignment software package], the algorithm as described in Pearson et al., Proc. Natl. Acad. Sci. USA, 85: 2444-2448 (1988) [the algorithm is incorporated into a FASTA program in a GCG software package], and the like, which can be preferably used in a similar manner.

More preferable, substantially the same amino acid sequence as the amino acid sequence shown by SEQ ID NO:2 is an amino acid sequence having a homology of about 60% or more, preferably about 70% or more, more preferably about 80% or more, and particularly preferably about 90% or more, to the amino acid sequence shown by SEQ ID NO:2.

As substantially the identical activity, for example, liver protection (inhibition of liver damage) action, apoptosis (hepatocyte death) inhibitory action, liver regeneration (differentiation and/or division of hepatocyte)-inducing action and the like can be mentioned. "Substantially the identical" means that these activities are qualitatively (e.g., physiologically or pharmacologically) the same. Therefore, the activities such as liver protection action, apoptosis inhibitory action and liver regeneration-inducing action are preferably equivalent (e.g., about 0.5- to about 2-fold), but quantitative factors such as the extent of activity and protein molecular weight may be different.

Measurement of the activities such as liver protection action, apoptosis inhibitory action and liver regeneration-inducing action can be performed according to a method known per se, which can include, but is not limited to, for example, methods as described in the below-mentioned Example such as histophathological observation (e.g., hematoxylin-eosin (H-E) stain), TUNEL assay, and immunohistochemistry using a proliferation marker such as Ki67 antigen as an index, of a liver tissue section, and the like, respectively.

HB-EGF of the present invention includes, for example, a protein containing (1) an amino acid sequence shown in SEQ ID NO:2 wherein one or more [preferably, about 1-50, preferably about 1-30, more preferably about 1-10, particularly preferably 1 to several (2, 3, 4 or 5)] amino acids have been deleted, (2) an amino acid sequence shown in SEQ ID NO:2 wherein one or more [preferably, about 1-50, preferably about 1-30, more preferably about 1-10, particularly preferably 1 to several (2, 3, 4 or 5)] amino acids have been added, (3) an amino acid sequence shown in SEQ ID NO:2 wherein one or more [preferably, about 1-50, preferably about 1-30, more preferably about 1-10, particularly preferably 1 to several (2, 3, 4 or 5)] amino acids have been inserted, (4) an amino acid sequence shown in SEQ ID NO:2 wherein one or more [preferably, about 1-50, preferably about 1-30, more preferably about 1-10, particularly preferably 1 to several (2, 3, 4 or 5)] amino acids have been substituted by other amino acids, or (5) an amino acid sequence wherein the above-mentioned sequences have been combined, and the like.

When an amino acid sequence is inserted, deleted or substituted as described above, the position of the insertion, deletion or substitution is not subject to limitation, as long as the protein retains its activity. As the position affecting the activity of HB-EGF can include, for example, an EGF-like domain (a region shown by amino acid numbers 105 to 148 in the amino acid sequence shown by SEQ ID NO:2), which is associated with binding with EGFR, a HB-EGF receptor, protease recognition and cleavage sites in shedding, and the like can be mentioned and, therefore, as the position of the insertion, deletion and substitution, for example, prosequence, C-terminal intracellular domain and the like can be mentioned. Alternatively, since it has been reported that heparin-binding domain (a region shown by amino acid numbers 93 to 105 in the amino acid sequence shown by SEQ ID NO:2) regulates binding activity of HB-EGF and EGFR negatively (J. Biol. Chem., 279(45): 47335-43 (2004)), the deletion, insertion and substitution in the domain can also maintain or enhance the activity of HB-EGF.

HB-EGF of the present invention is preferably human HB-EGF (GenBank Accession Number: NP_001936) having the amino acid sequence shown in SEQ ID NO:2, or an ortholog thereof in an other warm-blooded animal [for example, orthologs in mouse, rat, bovine, swine, Chinese hamster and chicken registered in Genbank under Accession Number NP_034545, NP_037077, XP_601210, NP_999464, AAD52998 and NP_990180 (having about 81%, about 82%, about 73%, about 91%, about 86% and about 73%, homology to human HB-EGF, respectively), respectively, and the like].

For the proteins and peptides mentioned herein, the left end is the N terminal (amino terminal) and the right end is the C terminal (carboxyl terminal) in accordance with the conventional peptide marking. Regarding HB-EGF of the present invention, including a protein comprising the amino acid sequence shown by SEQ ID NO:2, the C terminal may be any of a carboxyl group (—COOH), a carboxylate (—COO$^-$), an amide (—CONH$_2$), and an ester (—COOR).

Here, as R in the ester, a $C_{1-6}$ alkyl group such as methyl, ethyl, n-propyl, isopropyl, and n-butyl; a $C_{3-8}$ cycloalkyl group such as cyclopentyl and cyclohexyl; a $C_{6-12}$ aryl group such as phenyl and α-naphthyl; a phenyl-$C_{1-2}$ alkyl group such as benzyl and phenethyl; a $C_{7-14}$ aralkyl group such as an α-naphthyl-$C_{1-2}$ alkyl group such as α-naphthylmethyl; a pivaloyloxymethyl group; and the like are used.

When HB-EGF of the present invention has a carboxyl group (or a carboxylate) at a position other than the C terminal, a protein wherein the carboxyl group is amidated or esterified is also included in the protein of the present invention. In this case, as the ester, the above-described ester at the C terminal, and the like, for example, are used.

Furthermore, HB-EGF of the present invention also includes a protein wherein the amino group of the N terminal amino acid residue is protected by a protecting group (e.g., $C_{1-6}$ acyl groups such as $C_{1-6}$ alkanoyl groups such as formyl group and acetyl group; and the like), a protein wherein the N terminal glutamine residue, which is produced upon cleavage in vivo, has been converted to pyroglutamic acid, a protein wherein a substituent (e.g., —OH, —SH, amino group, imidazole group, indole group, guanidino group, and the like) on a side chain of an amino acid in the molecule is protected by an appropriate protecting group (e.g., $C_{1-6}$ acyl groups such as $C_{1-6}$ alkanoyl groups such as formyl group and acetyl group; and the like), a conjugated protein such as what is called a glycoprotein having a sugar chain bound thereto, and the like.

A HB-EGF partial peptide may be any peptide having the above-described HB-EGF partial amino acid sequence, and having substantially the same quality of activity as HB-EGF. Here, "substantially the same quality of activity" has the same definition as above. A measurement of "substantially the same quality of activity" can be conducted in the same manner as in the case of HB-EGF.

Specifically, as HB-EGF partial peptide, for example, in the amino acid sequence shown by SEQ ID NO:2, a partial amino acid sequence containing the EGF-like domain (mentioned above), which is associated with the binding with the receptor EGFR, a partial amino acid sequence containing a soluble HB-EGF (consisting of an amino acid sequence shown by amino acid numbers 63 to 148 in the amino acid sequence shown by SEQ ID NO:2), a partial amino acid sequence further having an intracellular domain (and a juxtamembrane/transmembrane domain) (consisting of an amino acid sequence shown by amino acid numbers 63 to 208 in the amino acid sequence shown by SEQ ID NO:2), and the like can be used.

As HB-EGF partial peptide, preferably a peptide having not less than 40 amino acids, more preferably not less than 80 amino acids, still more preferably not less than 140 amino acids, and the like can be used.

For HB-EGF partial peptide, the C terminal may be any of a carboxyl group (—COOH), a carboxylate (—COO⁻), an amide (—CONH$_2$), and an ester (—COOR). Here, as R in the ester, the same as those mentioned for HB-EGF above can be mentioned. When HB-EGF partial peptide has a carboxyl group (or a carboxylate) at a position other than the C terminal, a partial peptide wherein the carboxyl group is amidated or esterified is also included in HB-EGF partial peptide. In this case, as the ester, that similar to the ester at the C terminal, and the like, for example, are used.

Furthermore, HB-EGF partial peptide also includes a protein wherein the amino group of the N terminal amino residue is protected by a protecting group, a protein wherein glutamic residue at the N terminal in vivo has been converted to pyroglutamic acid, a protein wherein a substituent on a side chain of an amino acid in the molecule is protected by an appropriate protecting group, a conjugated peptide such as what is called a glycopeptide having a sugar chain bound thereto, and the like, as with the above-described HB-EGF.

As the salt of HB-EGF or a partial peptide thereof, physiologically acceptable salts with acid (e.g., inorganic acid, organic acid) or base (e.g., alkali metal) can be mentioned, and physiologically acceptable acid addition salts are preferred. Useful salts include, for example, salts with inorganic acids (e.g., hydrochloric acid, phosphoric acid, hydrobromic acid, sulfuric acid) or salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

HB-EGF or a salt thereof can be produced by a protein purification method known per se from the aforementioned cells or tissues of the warm-blooded animals. Specifically, HB-EGF or the salt thereof can be prepared by homogenizing the tissue or cell of the warm-blooded animal, then removing debris of the cell by low-speed centrifugation, precipitating a cellular membrane-containing fraction by high-speed centrifugation of a supernatant (as necessary, purifying the cellular membrane fraction by density gradient centrifugation and the like), and subjecting the fraction to a chromatography such as reversed-phase chromatography, ion exchange chromatography and affinity chromatography. When the soluble HB-EGF is prepared as HB-EGF partial peptide, it can be obtained by culturing the tissue or cell of the warm-blooded animal in a suitable medium, followed by subjecting a supernatant obtained by removing the cell by a filtration or centrifugation and the like to a chromatography such as reversed-phase chromatography, ion exchange chromatography and affinity chromatography.

HB-EGF or a partial peptide thereof or a salt thereof (hereinafter also comprehensively referred to as "HB-EGFs") can also be produced according to a publicly known method of peptide synthesis.

The method of peptide synthesis may be any of, for example, a solid phase synthesis process and a liquid phase synthesis process. A desired protein can be produced by condensing a partial peptide or amino acid capable of constituting HB-EGF with the remaining portion, and removing any protecting group the resultant product may have.

Here, the condensation and the protecting group removal are conducted in accordance with methods known per se, for example, the methods indicated in (i) to (v) below:
(i) M. Bodanszky and M. A. Ondetti: Peptide Synthesis, Interscience Publishers, New York (1966)
(ii) Schroeder and Luebke: The Peptide, Academic Press, New York (1965)
(iii) Nobuo Izumiya, et al.: Peptide Gosei-no-Kiso to Jikken (Basics and experiments of peptide synthesis), published by Maruzen Co. (1975);
(iv) Haruaki Yajima and Shunpei Sakakibara: Seikagaku Jikken Koza (Biochemical Experiment) 1, Tanpakushitsu no Kagaku (Chemistry of Proteins) IV, 205 (1977)
(v) Yoshiaki Kiso and Akira Otaka: Zoku Iyakuhin no Kaihatsu, Vol. 14, Peptide Synthesis, published by Hirokawa Shoten (1991).

The thus-obtained protein (peptide) can be purified and isolated by a publicly known method of purification. Here, as examples of the method of purification, solvent extraction, distillation, column chromatography, liquid chromatography, recrystallization, a combination thereof, and the like can be mentioned.

When the protein (peptide) obtained by the above-described method is a free form, it can be converted to an appropriate salt by a publicly known method or a method based thereon; conversely, when the protein (peptide) is obtained in the form of a salt, the salt can be converted to a free form or another salt by a publicly known method or a method based thereon.

For the synthesis of HB-EGF, an ordinary commercially available resin for protein synthesis can be used. As examples of such resins, chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenylacetamidomethyl resin, polyacrylamide resin, 4-(2',4'-dimethoxyphenyl-hydroxymethyl)phenoxy resin, 4-(2',4'-dimethoxyphenyl-Fmoc-aminoethyl)phenoxy resin and the like can be mentioned. Using such a resin, an amino acid having an appropriately protected α-amino group and side chain functional group is condensed on the resin in accordance with the sequence of the desired protein (peptide) according to one of various methods of condensation known per se. At the end of the reaction, the protein or the like is cleaved from the resin and at the same time various protecting groups are removed, and a reaction to form an intramolecular disulfide bond is carried out in a highly diluted solution to obtain the desired protein (peptide) or an amide thereof.

For the above-described condensation of protected amino acids, various activation reagents which can be used for protein synthesis can be used, and a carbodiimide is preferably used. As the carbodiimide, DCC, N,N'-diisopropyl-carbodiimide, N-ethyl-N'-(3-dimethylaminopropyl)carbodiimide and the like are used. For the activation using these carbodiimides, the protected amino acid, along with a racemation-suppressing additive (e.g., HOBt, HOOBt), may be added directly to the resin, or the protected amino acid may be activated in advance as a symmetric acid anhydride or HOBt ester or HOOBt ester and then added to the resin.

Solvents used for the activation of protected amino acids and condensation thereof with a resin can be appropriately selected from among solvents that are known to be usable for protein condensation reactions. As examples of useful solvents, acid amides such as N,N-dimethylformamide, N,N-dimethylacetamide and N-methylpyrrolidone; halogenated hydrocarbons such as methylene chloride and chloroform; alcohols such as trifluoroethanol; sulfoxides-such as dimethyl sulfoxide; amines such as pyridine; ethers such as dioxane and tetrahydrofuran; nitriles such as acetonitrile and propionitrile; esters such as methyl acetate and ethyl acetate; suitable mixtures thereof; and the like can be mentioned. Reaction temperature is appropriately selected from the range that is known to be usable for protein binding reactions, and is normally selected from the range of about −20° C. to about 50° C. An activated amino acid derivative is normally used from 1.5 to 4 times in excess. When a test using the ninhydrin reaction reveals that the condensation is insufficient, sufficient condensation can be conducted by repeating the condensation reaction without elimination of protecting groups. If the condensation is insufficient even though the reaction is repeated, unreacted amino acids may be acetylated using acetic anhydride or acetylimidazole.

A protecting method and a protecting group for a functional group that should not be involved in the reaction of raw materials, a method of removing the protecting group, a method of activating a functional group involved in the reaction, and the like can be appropriately selected from among publicly known groups or publicly known means.

As examples of the protecting group for an amino group of the starting material, Z, Boc, tertiary pentyloxycarbonyl, isobornyloxycarbonyl, 4-methoxybenzyloxycarbonyl, Cl-Z, Br—Z, adamantyloxycarbonyl, trifluoroacetyl, phthaloyl, formyl, 2-nitrophenylsulfenyl, diphenylphosphinothioyl, Fmoc, and the like can be used.

A carboxyl group can be protected, for example, by alkyl esterification (e.g., linear, branched or cyclic alkyl esterification with methyl, ethyl, propyl, butyl, tertiary butyl, cyclopentyl, cyclohexyl, cycloheptyl, cyclooctyl, 2-adamantyl, and the like), aralkyl esterification (e.g., benzyl esterification, 4-nitrobenzyl esterification, 4-methoxybenzyl esterification, 4-chlorobenzyl esterification, benzhydryl esterification), phenacyl esterification, benzyloxycarbonyl hydrazidation, tertiary butoxycarbonyl hydrazidation, trityl hydrazidation, and the like.

The hydroxyl group of serine can be protected by, for example, esterification or etherification. As examples of a group suitable for this esterification, lower alkanoyl groups such as an acetyl group, aroyl groups such as a benzoyl group, and groups derived from carbonic acid such as a benzyloxycarbonyl group and an ethoxycarbonyl group, and the like are used. As examples of a group suitable for etherification, a benzyl group, a tetrahydropyranyl group, a t-butyl group, and the like can be mentioned.

As examples of the protecting group for the phenolic hydroxyl group of tyrosine, Bzl, $Cl_2$-Bzl, 2-nitrobenzyl, Br—Z, tertiary butyl, and the like can be used.

As examples of the protecting group for the imidazole of histidine, Tos, 4-methoxy-2,3,6-trimethylbenzenesulfonyl, DNP, benzyloxymethyl, Bum, Boc, Trt, Fmoc, and the like are used.

As examples of the method of removing (eliminating) a protecting group, catalytic reduction in a hydrogen stream in the presence of a catalyst such as Pd-black or Pd-carbon; acid treatment by means of anhydrous hydrogen fluoride, methanesulfonic acid, trifluoromethane-sulfonic acid, trifluoroacetic acid, or a mixture solution thereof; base treatment by means of diisopropylethylamine, triethylamine, piperidine, piperazine or the like; and reduction with sodium in liquid ammonia, and the like are used. The elimination reaction by the above-described acid treatment is generally carried out at a temperature of about −20° C. to about 40° C.; the acid treatment is efficiently conducted by adding a cation scavenger, for example, anisole, phenol, thioanisole, m-cresol, p-cresol, dimethylsulfide, 1,4-butanedithiol and 1,2-ethanedithiol. Also, a 2,4-dinitrophenyl group used as a protecting group of the imidazole of histidine is removed by thiophenol treatment; a formyl group used as a protecting group of the indole of tryptophan is removed by acid treatment in the presence of 1,2-ethanedithiol, 1,4-butanedithiol, or the like, as well as by alkali treatment with a dilute sodium hydroxide solution, dilute ammonia, or the like.

As examples of those obtained by activation of the carboxyl group in the starting material, a corresponding acid anhydride, an azide, an activated ester [an ester with an alcohol (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, or HOBt)] and the like are used. As examples of those obtained by activation of the amino group in the starting material, a corresponding phosphoric amide is used.

In another method of preparing an amide of a protein (peptide), for example, the α-carboxyl group of the carboxy terminal amino acid is first amidated and hence protected, and a peptide chain is elongated to a desired chain length toward the amino group side, thereafter a protein (peptide) having the protecting group for the N terminal α-amino group of the peptide chain only removed and a protein (peptide) having the protecting group for the C terminal carboxyl group only removed are prepared, and these proteins or the like are condensed in a mixed solvent described above. For details about the condensation reaction, the same as above applies. After the protected protein (protected peptide) obtained by the condensation is purified, all protecting groups can be removed by the above-described method to yield a desired crude protein (crude peptide). By purifying this crude protein (crude peptide) using various publicly known means of purification, and freeze-drying the main fraction, a desired amide of the protein (peptide) can be prepared.

For esters of the protein (peptide), a desired ester of the protein or the like can be prepared by, for example, condensing the α-carboxyl group of the carboxy terminal amino acid with a desired alcohol to yield an amino acid ester, and then treating the ester in the same manner as with an amide of the above-mentioned protein (peptide).

HB-EGF partial peptide or a salt thereof can also be produced by cleaving HB-EGF or a salt thereof with an appropriate peptidase (e.g., ADAM9, ADAM12, etc.)

Furthermore, HB-EGF can also be produced by cultivating a transformant comprising nucleic acid encoding HB-EGF or a partial peptide thereof, and separating and purifying HB-EGF from the culture obtained. The nucleic acid encoding HB-EGF or a partial peptide thereof can be DNA or RNA, or DNA/RNA chimera. Preferably DNA can be mentioned. Also, the nucleic acid can be double stranded or single stranded. When it is double stranded, it can be double stranded DNA, double stranded RNA or DNA:RNA hybrid. When it is single stranded, it can be sense strand (i.e., coding strand) or antisense strand (i.e., non-coding strand).

As the DNA encoding HB-EGF or a partial peptide thereof, genomic DNA, cDNA (cRNA) derived from a cell [for example, hepatocyte, splenocyte, nerve cell, glial cell, pancreatic β cell, bone marrow cell, mesangial cell, Langerhans cell, epidermal cell, epithelial cell, goblet cell, endothelial cell, smooth muscle cell, fibroblast, fiber cell, muscle cell, adipocyte, immune cell (e.g., macrophage, T cell, B cell, natural killer cell, mast cell, neutrophil, basophil, eosinophil, monocyte), megakaryocyte, synovial cell, chondrocyte, osteocyte, osteoblast, osteoclast, mammary cell or interstitial cell, or precursor cell, stem cell, established or cancer cell thereof, and the like] of human or other warm-blooded animal (e.g., monkey, bovine, horse, swine, sheep, goat, rabbit, mouse, rat, guinea pig, hamster, chicken and the like) or any tissue or organ in which these cells are present [for example, olfactory bulb, amygdaloid nucleus, basal ganglia, hippocampus, thalamus, hypothalamus, cerebral cortex, medulla oblongata, cerebellum), spinal cord, pituitary gland, stomach, pancreas, kidney, liver, gonad, thyroid gland, gall bladder, bone marrow, adrenal gland, skin, muscle, lung, gastrointestinal tract (e.g., large intestine, small intestine), blood vessel, heart, thymus, spleen, submandibular gland, peripheral blood, prostate, orchis, ovary, placenta, uterus, bone, joint, adipose tissue (e.g., brown adipose tissue, white adipose tissue), skeletal muscle and the like], synthetic DNA (RNA) and the like can be mentioned. The genomic DNA and cDNA encoding HB-EGF or a partial peptide thereof can be directly amplified by Polymerase Chain Reaction (hereinafter to be abbreviated as "PCR method") and Reverse Transcriptase-PCR (hereinafter to be abbreviated as "RT-PCR method") using a genomic DNA fraction and total RNA or mRNA fraction prepared from the above-mentioned cell/tissue as templates, respectively. Alternatively, the genomic DNA and cDNA encoding HB-EGF or a partial peptide thereof can be cloned by colony or plaque hybridization method, or PCR method and the like, from a genome DNA library and cDNA library prepared by inserting a fragment of genomic DNA and total RNA or mRNA prepared from the above-mentioned cell/tissue into a suitable vector. The vector used for the library may be any of a bacteriophage, a plasmid, a cosmid, a phagemid and the like.

As examples of the nucleic acids encoding HB-EGF, nucleic acids containing a base sequence represented by SEQ ID NO:1 (with the proviso that when the nucleic acid is RNA, "t" in the base sequence is to be read as "u"), nucleic acids containing a base sequence capable of hybridizing to a complementary strand sequence of the base sequence represented by SEQ ID NO:1 under stringent conditions, and encoding a protein having substantially the identical activity to HB-EGF mentioned above [e.g.: binding activity to EGFR, liver protection (inhibition of liver damage) action, apoptosis (hepatocyte death) inhibitory action, liver regeneration (differentiation and/or division of hepatocyte)-inducing action and the like], and the like can be mentioned.

The nucleic acids capable of hybridizing to a complementary strand sequence of the base sequence represented by SEQ ID NO:1 under stringent conditions used include, for example, nucleic acids containing a base sequence having not less than about 60%, preferably not less than about 70%, more preferably not less than about 80%, and particularly preferably not less than about 90%, homology to the base sequence represented by SEQ ID NO:1, and the like.

The homology of the base sequence in the present specification can be calculated using homology calculation algorithm NCBI BLAST (National Center for Biotechnology Information Basic Local Alignment Search Tool) under the following conditions (expectancy=10; allowing gap; filtering=ON; match score=1; mismatch score=−3). Examples of other algorithms to determine a homology of base sequence preferably include the above-mentioned homology calculation algorithms of amino acid sequence in a similar manner.

Hybridization can be conducted according to a method known per se or a method based thereon, for example, a method described in Molecular Cloning, 2nd edition (J. Sambrook et al., Cold Spring Harbor Lab. Press, 1989) and the like. When a commercially available library is used, hybridization can be conducted according to the method described in the instruction manual attached thereto. Hybridization can preferably be conducted under highly stringent conditions.

The stringent conditions are exemplified by reaction conditions characterized in that (1) a low ionic strength and a high temperature, for example, 0.015 M sodium chloride/0.0015 M sodium citrate/0.1% dodecyl sodiumsulfate at 50° C., is used for washing, and (2) a denaturing agent such as formamide, for example, 50% (v/v) formamide along with a 50 mM sodium phosphate buffer (pH 6.5) containing 0.1% bovine serum albumin/0.1% Ficoll/0.1% polyvinylpyrrolidone/750 mM sodium chloride and 75 mM sodium citrate is used at 42° C. Alternatively, the stringent condition can be a condition in which 50% formamide, 5×SSC (0.75 M NaCl, 0.075 M sodium citrate), 50 mM sodium phosphate (pH 6.8), 0.1% sodium pyrophosphate, 5× Denhart's solution, sonicated salmon sperm DNA (50 μg/ml), 0.1% SDS, and 10% dextran sulfate are used at 42° C., and a washing is performed with 0.2×SSC and 50% formaldehyde at 55° C., followed by a high-stringent washing comprised of EDTA-containing 0.1×SSC at 55° C. Those of ordinary skill in the art can easily achieve a desired stringency by appropriately adjusting temperature at hybridization reaction and/or washing, ion strength of buffer, and the like based on factors such as probe length.

The nucleic acid encoding HB-EGF is, preferably, a nucleic acid containing a base sequence encoding human HB-EGF shown by a base sequence represented by SEQ ID NO:1 (GenBank Accession Number: NM_001945), or an ortholog thereof in an other warm-blooded animal [for example, orthologs in mouse, rat, bovine, swine, Chinese hamster and chicken registered in GenBank under Accession Number NM_010415, NM_012945, XM_601210, NM_214299, AF069753 and NM_204849 (having about 83%, about 83%, about 74%, about 88%, about 74% and about 63%, homology to human HB-EGF cDNA, respectively), respectively, and the like].

The nucleic acid encoding HB-EGF partial peptide of the present invention may be any one comprising the base sequence encoding the same or substantially the same amino acid sequence as a portion of the amino acid sequence shown by SEQ ID NO:2. The DNA may be any of genomic DNA, cDNA derived from the above-described cell or tissue, a cDNA (cRNA) derived from the above-described cell or tissue, and synthetic DNA (RNA). The vector used for the library may be any of a bacteriophage, a plasmid, a cosmid, a phagemid and the like. The DNA can also be amplified directly by the RT-PCR method using an mRNA fraction prepared from the above-described cell or tissue.

Specifically, as the nucleic acid encoding HB-EGF partial peptide, for example, (1) a nucleic acid having a partial base sequence of the base sequence represented by SEQ ID NO:1, (2) a nucleic acid containing a base sequence hybridizing to a nucleic acid having the base sequence represented by SEQ ID NO:1 under stringent conditions, and encoding a peptide having the substantially the identical activity to HB-EGF [e.g.: binding activity to EGFR, liver protection (inhibition of liver damage) action, apoptosis (hepatocyte death) inhibitory action, liver regeneration (differentiation and/or division of hepatocyte)-inducing action and the like] mentioned above, or the like is used.

As examples of the DNA capable of hybridizing to the base sequence shown by SEQ ID NO:1 under stringent conditions, a nucleic acid comprising a base sequence showing a homology of about 60% or more, preferably about 70% or more, more preferably about 80% or more, and particularly preferably about 85% or more, to the base sequence, and the like are used.

The DNA encoding HB-EGF or a partial peptide thereof can be cloned by amplifying it by the PCR method using a synthetic DNA primer comprising a portion of the base sequence encoding HB-EGF or a partial peptide thereof, or by hybridizing DNA incorporated in an appropriate expression vector to a labeled DNA fragment or synthetic DNA encoding a portion or the entire region of HB-EGF protein. Hybridization can be conducted according to, for example, a method described in Molecular Cloning, 2nd edition (ibidem) and the like. When a commercially available library is used, hybridization can be conducted according to the method described in the instruction manual attached to the library.

The base sequence of DNA can be converted according to a method known per se, such as the ODA-LA PCR method, the Gapped duplex method, the Kunkel method and the like, or a method based thereon, using a publicly known kit, for example, Mutan™-super Express Km (Takara Shuzo Co., Ltd.), Mutan™-K (Takara Shuzo Co., Ltd.) and the like.

The cloned DNA can be used as is, or after digestion with a restriction endonuclease or addition of a linker as desired, depending on the purpose of its use. The DNA may have the translation initiation codon ATG at the 5' end thereof, and the translation stop codon TAA, TGA or TAG at the 3' end thereof. These translation initiation codons and translation stop codons can be added using an appropriate synthetic DNA adapter.

An expression vector containing DNA encoding HB-EGF or a partial peptide thereof can be produced by, for example, cutting out a desired DNA fragment from the DNA encoding HB-EGF, and joining the DNA fragment downstream of a promoter in an appropriate expression vector.

Useful expression vectors include plasmids derived from *Escherichia coli* (e.g., pBR322, pBR325, pUC12, pUC13); plasmids derived from *Bacillus subtilis* (e.g., pUB110, pTP5, pC194); plasmids derived from yeast (e.g., pSH19, pSH15); insect cell expression plasmids (e.g., pFast-Bac); animal cell expression plasmids (e.g., pA1-11, pXT1, pRc/CMV, pRc/RSV, pcDNAI/Neo); bacteriophages such as λ phage; insect viral vectors such as baculovirus (e.g., BmNPV, AcNPV); animal viral vectors such as retrovirus, vaccinia virus, adenovirus and adeno-associated virus; and the like.

The promoter may be any promoter, as long as it is appropriate for the host used to express the gene.

For example, when the host is an animal cell, useful promoters include promoters derived from cytomegalovirus (CMV) (e.g., CMV immediate-early promoter), promoters derived from human immunodeficiency virus (HIV) (e.g., HIV LTR), promoters derived from Rous sarcoma virus (RSV) (e.g., RSV LTR), promoters derived from mouse mammary cancer virus (MMTV) (e.g., MMTV LTR), promoters derived from Moloney murine leukemia virus (MOMLV) (e.g., MOMLV LTR), promoters derived from herpes simplex virus (HSV) (e.g., HSV thymidine kinase (TK) promoter), promoters derived from SV40 (e.g., SV40 early promoter), promoters derived from Epstein-Barr virus (EBV), promoters derived from adeno-associated virus (AAV) (e.g., AAV p5 promoter), promoters derived from adenovirus (AdV) (Ad2 or Ad5 major late promoter) and the like.

When the host is a bacterium of the genus *Escherichia*, the trp promoter, the lac promoter, the recA promoter, the XPL promoter, the lpp promoter, the T7 promoter and the like are preferred.

When the host is a bacterium of the genus *Bacillus*, the SPO1 promoter, the SPO2 promoter, the penP promoter and the like are preferred.

When the host is yeast, the PHO5 promoter, the PGK promoter, the GAP promoter, the ADH promoter and the like are preferred.

When the host is an insect cell, the polyhedrin promoter, the P10 promoter and the like are preferred.

Useful expression vectors include, in addition to the above, those optionally harboring an enhancer, a splicing signal, a polyA addition signal, a selection marker, an SV40 replication origin and the like. As examples of the selection marker, the dihydrofolate reductase (dhfr) gene [methotrexate (MTX) resistance], the ampicillin resistance (Amp$^r$) gene, the neomycin resistance (Neo$^r$) gene (G418 resistance) and the like can be mentioned. In particular, when a dhfr-deficient Chinese hamster (CHO-dhfr$^-$) cell is used in combination with the dhfr gene as the selection marker, a target gene can also be selected using a thymidine-free medium.

Where necessary, a base sequence encoding a signal sequence (signal codon) suitable for the host can be added to the 5'-end side of the DNA encoding HB-EGF or a partial peptide thereof. When the host is a bacterium of the genus *Escherichia*, useful sequences include PhoA signal sequence, OmpA-signal sequence and the like; when the host is a bacterium of the genus *Bacillus*, useful sequences include α-amylase signal sequence, subtilisin•signal sequence and the like; when the host is yeast, useful sequences include MFα•signal sequence, SUC2•signal sequence and the like; and when the host is an animal cell, useful sequences include insulin•signal sequence, α-interferon•signal sequence, antibody molecule-signal sequence and the like.

Useful hosts include, for example, a bacterium of the genus *Escherichia*, a bacterium of the genus *Bacillus*, yeast, an insect cell, an insect, an animal cell and the like.

Useful bacteria of the genus *Escherichia* include, for example, *Escherichia coli* K12, DH1, JM103, JA221, HB101, C600 and the like.

Useful bacteria of the genus *Bacillus* include, for example, *Bacillus subtilis* M1114, 207-21 and the like.

Useful yeasts include, for example, *Saccharomyces cerevisiae* AH22, AH22R$^-$, NA87-11A, DKD-5D and 20B-12, *Schizosaccharomyces pombe* NCYC1913 and NCYC2036, *Pichia pastoris* KM71, and the like.

Useful insect cells include, for example, *Spodoptera frugiperda* cell (Sf cell), MG1 cell derived from the mid-intestine of *Trichoplusia ni*, High Five™ cell derived from an egg of *Trichoplusia ni*, cell derived from *Mamestra brassicae*, cell derived from *Estigmena acrea*, and the like can be mentioned when the virus is AcNPV. When the virus is BmNPV, useful insect cells include *Bombyx mori* N cell (BmN cell) and the like. Useful Sf cells include, for example, Sf9 cell (ATCC CRL1711), Sf21 cell (both in Vaughn, J. L. et al., In Vivo, 13, 213-217 (1977) and the like.

Useful insects include, for example, a larva of *Bombyx mori* and the like.

Useful animal cells include, for example, cell derived from a monkey (e.g., COS-1, COS-7, CV-1, Vero), cell derived from a hamster (e.g., BHK, CHO, CHO-K1, CHO-dhfr⁻), cell derived from a mouse (e.g., NIH3T3, L, L929, CTLL-2, AtT-20), cell derived from a rat (e.g., H4IIE, PC-12, 3Y1, NBT-II), cell derived from a human (e.g., HEK293, A549, HeLa, HepG2, HL-60, Jurkat, U937) and the like.

Transformation can be carried out according to the kind of host in accordance with a publicly known method.

A bacterium of the genus *Escherichia* can be transformed, for example, in accordance with a method described in Proc. Natl. Acad. Sci. U.S.A., Vol. 69, 2110 (1972), Gene, Vol. 17, 107 (1982) and the like.

A bacterium of the genus *Bacillus* can be transformed, for example, according to a method described in Molecular and General Genetics, Vol. 168, 111 (1979) and the like.

Yeast can be transformed, for example, in accordance with a method described in Methods in Enzymology, Vol. 194, 182-187 (1991), Proc. Natl. Acad. Sci. USA, Vol. 75, 1929 (1978) and the like.

An insect cell and an insect can be transformed, for example, according to a method described in Bio/Technology, 6, 47-55 (1988) and the like.

An animal cell can be transformed, for example, in accordance with a method described in Saibo Kogaku (Cell Engineering), extra issue 8, Shin Saibo Kogaku Jikken Protocol (New Cell Engineering Experimental Protocol), 263-267 (1995), published by Shujunsha, or Virology, Vol. 52, 456 (1973).

HB-EGF can be separated and purified from the culture obtained by cultivating the aforementioned transformant according to a method known per se.

For example, when HB-EGF is extracted from a cultured bacterium or a cell cytoplasm, a method is used as appropriate wherein bacteria or cells are collected from a culture by a known means, suspended in an appropriate buffer solution, and disrupted by means of sonication, lysozyme and/or freeze-thawing and the like, after which a crude extract of soluble protein is obtained by centrifugation or filtration. The buffer solution may contain a protein denaturant such as urea or guanidine hydrochloride and a surfactant such as Triton X-100™ (when the surfactant is contained, some or all of membrane proteins and organelle proteins can be simultaneously extracted). On the other hand, when HB-EGF are extracted from a membrane fraction, a method is used wherein bacteria or cells are disrupted in the same manner as mentioned above, after which a debris of the cells is precipitated and removed by low-speed centrifugation, a supernatant is subjected to high-speed centrifugation to precipitate membrane-containing fraction (as necessary, cellular membrane fraction, mitochondrial fraction, nucleus fraction and the like can be separated and purified by density gradient centrifugation and the like), and the like. When HB-EGF are secreted out of bacteria (cells), a method is used wherein a culture supernatant is sorted from a culture by centrifugation, filtration or the like, and the like.

Isolation and purification of HB-EGF contained in the thus-obtained soluble fraction, membrane fraction or culture supernatant can be conducted according to a method know per se. Useful methods include methods based on solubility, such as salting-out and solvent precipitation; methods based mainly on molecular weight differences, such as dialysis, ultrafiltration, gel filtration, and SDS-polyacrylamide gel electrophoresis; methods based on charge differences, such as ion exchange chromatography; methods based on specific affinity, such as affinity chromatography; methods based on hydrophobicity differences, such as reversed-phase high performance liquid chromatography; and methods based on isoelectric point differences, such as isoelectric focusing electrophoresis. These methods can be combined as appropriate.

When the thus-obtained HB-EGF or a partial peptide thereof is a free form, it can be converted to a salt by a method known per se or a method based thereon; when the protein or peptide is obtained as a salt, it can be converted to a free form or another salt by a method known per se or a method based thereon.

Note that HB-EGF produced by the transformant can also be optionally modified by the action of an appropriate protein-modifying enzyme, before or after purification, or can have a polypeptide thereof removed partially. As such, useful protein-modifying enzymes include, for example, trypsin, chymotrypsin, arginyl endopeptidase, protein kinase, glycosidase and the like.

The presence of the thus-obtained HB-EGF can be confirmed by enzyme immunoassay, Western blotting and the like using an antibody specific thereto.

Furthermore, HB-EGF or a partial peptide thereof can also be synthesized by in vitro translation using a cell-free protein translation system comprising a rabbit reticulocyte lysate, wheat germ lysate, *Escherichia coli* lysate and the like, with RNA corresponding to the above-described DNA encoding HB-EGF or a partial peptide thereof as the template. Alternatively, HB-EGF or a partial peptide thereof can be synthesized using a cell-free transcription/translation system further containing RNA polymerase, with the DNA encoding HB-EGF or a partial peptide thereof as the template. As the cell-free protein transcription/translation system, commercially available one may be used, or may also be prepared by a method known per se; specifically, *Escherichia coli* extract can be prepared according to the methods described in Pratt, J. M. et al., Transcription and Translation, Hames, B. D. and Higgins, S. J. eds., IRL Press, Oxford 179-209 (1984), and the like. As commercially available cell lysates, those derived from *Escherichia coli* include E. coli S30 extract system (manufactured by Promega), RTS 500 Rapid Translation System (manufactured by Roche) and the like; those derived from rabbit reticulocyte include Rabbit Reticulocyte Lysate System (manufactured by Promega) and the like: and furthermore, those derived from wheat germ include PROTEIOS™ (manufactured by TOYOBO) and the like. Of these, cell lysates using a wheat germ lysate are preferable. Examples of the production method of a wheat germ lysate include the methods described in Johnston, F. B. et al., Nature, 179: 160-161 (1957), Erickson, A. H. et al., Meth. Enzymol., 96: 38-50 (1996) and the like.

Useful systems or apparatuses for protein synthesis include the batch method (Pratt, J. M. et al. (1984) mentioned above), continuous cell-free protein synthesis system (Spirin, A. S. et al., Science, 242: 1162-1164 (1988)) wherein amino acids, energy source and the like are continuously supplied to a reaction system, dialysis (Kigawa et al., 21st Annual Meeting of the Molecular Biology Society of Japan, WID6), the overlay method (instruction manual of PROTEIOS™ Wheat germ cell-free protein synthesis core kit: manufactured by TOYOBO) and the like. Useful methods additionally include one wherein template RNAS, amino acids, energy sources and the like are supplied to a synthesis reaction system when needed, and synthetic substances and decomposed substances are discharged when needed (JP-A-2000-333673), and the like.

HB-EGF exhibits liver protection (inhibition of liver damage) action, apoptosis (hepatocyte death) inhibitory action, liver regeneration (differentiation and/or division of hepatocyte)-inducing action and the like; therefore, HB-EGF, or nucleic acids encoding HB-EGF or a partial peptide thereof can be applied as an agent for protecting the liver, an inhibitor of hepatocyte apoptosis and a liver regeneration promoter, and can be used for the prophylaxis/treatment of liver diseases such as liver damage and various diseases associated with hepatocyte death, for example, acute liver damage (fulminant hepatic failure, acute hepatitis, drug-induced hepatitis), chronic hepatitis, autoimmune liver disease (autoimmune hepatitis, primary biliary cirrhosis), viral hepatitis (type A-E), liver fibrosis, cirrhosis, liver carcinoma, alcoholic liver disease, drug-induced liver disease (toxic drug-induced liver disease, allergic drug-induced liver disease), liver abscess, hepatic parasitosis (schistosomiasis Japonica, clonorchiasis), hepatic amyloidosis, lupoid hepatitis) and the like, in a hepatectomy, or in promoting liver regeneration after a liver transplantation.

(1) An Agent Containing HB-EGF for Protecting the Liver/Promoting Liver Regeneration Since an agent for protecting the liver or promoting liver regeneration containing HB-EGF provides effect in several hours after administration, it can be preferably used for acute liver diseases, particularly acute liver diseases accompanied by hepatocyte apoptosis due to inflammation. However, it can also be preferably used as an agent for the prophylaxis/inhibition of progression, which aims at preventing exhaustion of hepatocytes and cell death associated with chronic diseases such as chronic hepatitis, liver fibrosis and cirrhosis by, as described below, improving the stability by taking the dosage form of a sustained release preparation or forming an immunoconjugate with an antibody.

HB-EGF can be used as it is, or may be mixed with a pharmacologically acceptable carrier as necessary to form a pharmaceutical composition and used as a pharmaceutical agent mentioned above.

Here, as examples of the pharmacologically acceptable carrier, various organic or inorganic carrier substances conventionally used as pharmaceutical preparation materials can be mentioned, and these are formulated as excipients, lubricants, binders and disintegrants, in solid preparations; as solvents, solubilizing agents, suspending agents, isotonizing agents, buffering agents and soothing agents, in liquid preparations, and the like. Also, as necessary, pharmaceutical preparation additives such as antiseptics, antioxidants, colorants, sweeteners and the like can be used.

As examples of suitable excipients, lactose, saccharose, D-mannitol, D-sorbitol, starch, gelatinized starch, dextrin, crystalline cellulose, low substituted hydroxypropyl cellulose, sodium carboxymethyl cellulose, gum arabic, pullulan, light anhydrous silicic acid, synthetic aluminum silicate, magnesium aluminometasilicate and the like can be mentioned.

As examples of suitable lubricants, magnesium stearate, calcium stearate, talc, colloidal silica and the like can be mentioned.

As examples of suitable binders, gelatinized starch, sucrose, gelatin, gum arabic, methyl cellulose, carboxymethyl cellulose, sodium carboxymethyl cellulose, crystalline cellulose, saccharose, D-mannitol, trehalose, dextrin, pullulan, hydroxypropyl cellulose, hydroxypropylmethyl cellulose, polyvinyl pyrrolidone and the like can be mentioned.

As examples of suitable disintegrants, lactose, saccharose, starch, carboxymethyl cellulose, calcium carboxymethyl cellulose, sodium crosscarmellose, sodium carboxymethyl starch, light anhydrous silicic acid, low substituted hydroxypropyl cellulose and the like can be mentioned.

As examples of suitable solvents, water for injection, physiological saline, Ringer's solutions, alcohols, propylene glycol, polyethylene glycol, sesame oil, corn oil, olive oil, cottonseed oil and the like can be mentioned.

As examples of suitable solubilizing agents, polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like can be mentioned.

As examples of suitable suspending agents, surfactants such as stearyl triethanolamine, sodium lauryl sulfate, lauryl aminopropionic acid, lecithin, benzalkonium chloride, benzethonium chloride and glyceryl monostearate; hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose; polysorbates, polyoxyethylene hardened castor oil and the like can be mentioned.

As examples of suitable isotonizing agents, sodium chloride, glycerin, D-mannitol, D-sorbitol, glucose and the like can be mentioned.

As examples of suitable buffers, buffer solutions of a phosphate, an acetate, a carbonate, a citrate and the like, and the like can be mentioned.

As examples of suitable soothing agents, benzyl alcohol and the like can be mentioned.

As examples of suitable antiseptics, paraoxybenzoates, chlorobutanol, benzyl alcohol, phenethyl alcohol, dehydroacetic acid, sorbic acid and the like can be mentioned.

As examples of suitable antioxidants, sulfides, ascorbates and the like can be mentioned.

As examples of suitable colorant s, aqueous food tar colors (e.g., food colors such as Food Red Nos. 2 and 3, Food Yellow Nos. 4 and 5, and Food Blue Nos. 1 and 2), water-insoluble lake pigments (e.g., aluminum salts of the aforementioned aqueous food tar colors and the like), natural pigments (e.g., β-carotene, chlorophyll, red iron oxide and the like) and the like can be mentioned.

As examples of suitable sweeteners, sodium saccharide, dipotassium glycyrrhizinate, aspartame, stevia and the like can be mentioned.

As examples of dosage forms of the aforementioned pharmaceutical composition, oral formulations such as tablets, capsules (including soft capsules and microcapsules), granules, powders, syrups, emulsions and suspensions; non-oral formulations such as injections (e.g., subcutaneous injections, intravenous injections, intramuscular injections, intraperitoneal injections and the like), external formulations (e.g., nasal preparations, transdermal preparations, ointments and the like), suppositories (e.g., rectal suppositories, vaginal suppositories and the like), pellets, drops, sustained-release preparations (e.g., sustained-release microcapsules and the like) and the like can be mentioned.

The pharmaceutical composition can be produced by a method conventionally used in the field of pharmaceutical preparation making, for example, a method described in the Japanese Pharmacopoeia and the like. A specific method of producing a preparation is hereinafter described in detail. The content of active ingredient in the pharmaceutical composition varies depending on the dosage form, the dose of the active ingredient and the like; and is, for example, from about 0.1 to 100% by weight.

For example, an oral formulation is produced by adding to an active ingredient an excipient (e.g., lactose, saccharose, starch, D-mannitol and the like), a disintegrant (e.g., calcium carboxymethyl cellulose and the like), a binder (e.g., gelatinized starch, gum arabic, carboxymethyl cellulose, hydroxypropyl cellulose, polyvinyl pyrrolidone and the like), a lubricant (e.g., talc, magnesium stearate, polyethylene glycol 6000 and the like) and the like, compression molding the resultant mixture, and subsequently, as required, coating the resulting material with a coating base by a method known per se for the purpose of taste masking, enteric solubility or sustained release.

As examples of the coating base, a sugar-coating base, a aqueous film coating base, an enteric film coating base, a sustained-release film coating base and the like can be mentioned.

As the sugar-coating base, saccharose is used, which may be used in combination with one species or two or more species selected from among talc, precipitated calcium carbonate, gelatin, gum arabic, pullulan, carnauba wax and the like.

As examples of the aqueous film coating base, cellulose polymers such as hydroxypropyl cellulose, hydroxypropylmethyl cellulose, hydroxyethyl cellulose and methylhydroxyethyl cellulose; synthetic polymers such as polyvinylacetal diethylanimoacetate, aminoalkylmethacrylate copolymer E [Eudragit-E (trade name), Rohm Pharma Corp.] and polyvinyl pyrrolidone; polysaccharides such as pullulan; and the like can be mentioned.

As examples of the enteric film coating base, cellulose polymers such as hydroxypropylmethyl cellulose phthalate, hydroxypropylmethyl cellulose acetate succinate, carboxymethylethyl cellulose, and cellulose acetate phthalate; acrylic polymers such as Methacrylic Acid Copolymer L [Eudragit-L (trade name), Rohm Pharma Corp.], Methacrylic Acid Copolymer LD [Eudragit-L-30D55 (trade name), Rohm Pharma Corp.], and Methacrylic Acid Copolymer S [Eudragit-S (trade name), Rohm Pharma Corp.]; natural substances such as shellac, and the like can be mentioned.

As examples of the sustained-release film coating base, cellulose polymers such as ethyl cellulose; acrylic polymers such as aminoalkyl methacrylate copolymer RS [Eudragit-RS (trade name), Rohm Pharma Corp.], and an ethyl acrylate-methylmethacrylate copolymer suspension [Eudragit-NE (trade name), Rohm Pharma Corp.]; and the like can be mentioned.

The above-mentioned coating bases may also be used in a mixture of two or more kinds thereof in a suitable ratio. Also, during coating, a shading agent, for example, titanium oxide or iron sesquioxide, may be used.

Examples of preparations suitable for parenteral administration (e.g., subcutaneous injection, intramuscular injection, topical injection, intraperitoneal administration and the like) include aqueous and nonaqueous isotonic aseptic injection liquids, in which antioxidant, buffer, antiviral agent, isotonicity agent and the like can be contained. The examples also include aqueous and nonaqueous aseptic suspension liquids optionally containing suspension agent, solubilizer, thickener, stabilizer, preservative and the like. When the administration method is a topical injection around a target region, injectable liquids are preferable. Alternatively, a sustained-release preparation can be prepared by using a bioaffinity material such as collagen. Since the Pluronic gel turns into a gel at the body temperature, and is present in a liquid state at a temperature not higher than the body temperature, HB-EGF can be topically injected along with a Pluronic gel and gelatinized around a target tissue to achieve long-term sustainability. The protein preparation can be sealed in a container by a unit dose or plural doses like ampoules and vials. In addition, HB-EGF and a pharmaceutically acceptable carrier can be lyophilized and preserved such that they only need to be dissolved or suspended in a suitable aseptic vehicle immediately before use.

Since antibodies against a hepatocyte surface molecule can specifically deliver a pharmaceutical agent into a hepatocyte, stability of HB-EGF in blood and efficiency in delivery can be improved by preparing an immunoconjugate in which HB-EGF are crosslinked with the antibody. Examples of the hepatocyte surface molecules include, but not limited to, EGFR (HER1), HER2, HER3, HER4 and the like. When an anti-EGFR antibody is used, a nonneutralizing antibody is preferably used as an antibody for targeting so as not to inhibit signal transduction from EGFR.

Although the antibody against a hepatocyte surface molecule may be a polyclonal antibody or monoclonal antibody, a monoclonal antibody is preferred. The antibody can be produced by a well known immunological technique. The antibody may be a complete antibody molecule or a fragment. The fragment may be any, as long as it possesses an antigen binding site (CDR) to the hepatocyte surface molecule; examples include Fab, F(ab')$_2$, ScFv, minibody and the like.

The monoclonal antibody can be produced by cell fusion method (e.g., Takeshi Watanabe, *Saiboyugoho no Genri to Monoclonal-Kotai no Sakusei*, Akira Taniuchi, edited by Toshitada Takahashi, "*Monoclonal-Kotai to Gan-Kiso to Rinsho-*", 2-14, Science Forum Publishing, (1985)). For example, a mouse is administrated subcutaneously or intraperitoneally 2 to 4 times with a target protein (as necessary, the protein can be crosslinked with a carrier protein such as bovine serum albumin and KLH (Keyhole Limpet Hemocyanin) to form a complex) being an antigen along with a commercially available adjuvant, a spleen or lymph node is collected about 3 days after the final administration to collect leukocytes. The leukocytes and myeloma cells (e.g., NS-1, P3X63Ag8 and the like) are subjected to a cell fusion to give hybridomas that produce a monoclonal antibody against the factor. The cell fusion may be performed by the PEG method [*J. Immunol. Methods*, 81(2): 223-228 (1985)] or by the voltage pulse method [*Hybridoma*, 7(6): 627-633 (1988)]. A hybridoma that produces the desired monoclonal antibody can be selected by detecting an antibody that binds specifically to the antigen from the culture supernatant using a widely known EIA or RIA method and the like. Cultivation of the hybridoma that produces the monoclonal antibody can be performed in vitro, or in vivo such as in mouse or rat, preferably in mouse ascitic fluid, and the antibody can be acquired from the culture supernatant of the hybridoma and the ascitic fluid of the animal, respectively.

Considering administration to a human, however, the antibody is preferably a chimeric antibody of a human and another animal (e.g., mouse and the like), more preferably a humanized antibody, and most preferably a complete human antibody. "Chimeric antibody" herein refers to an antibody having an immunized animal-derived variable region (V region) and a human-derived constant region (C region), and "humanized antibody" refers to an antibody wherein all regions other than CDR are replaced with a human antibody. A chimeric antibody and humanized antibody can be acquired by, for example, cleaving out the sequence encoding the V region or CDR from a mouse monoclonal antibody gene prepared by the same method as described above, cloning a chimeric gene prepared by fusion of the sequence with the DNA encoding the C region of a human myeloma-derived antibody into an appropriate expression vector, and introducing this into an appropriate host cell to allow the chimeric gene to be expressed. A complete human antibody can be acquired by using a known phage display library, or by using a human antibody-producing mouse developed by Medarex, Inc. or a KM mouse jointly-developed by Medarex, Inc. and Kirin Inc..

Useful methods of crosslinking of an antibody against a hepatocyte surface molecule and HB-EGF include, but not limited to, the method described in *Adv. Drug Deliv. Rev.*, 53: 171-216 (2001).

An agent containing HB-EGF for protecting the liver/promoting liver regeneration, which has been designed to have the dosage form mentioned above, can be dissolved or suspended in a suitable aseptic vehicle and administered orally or parenterally to, for example, mammals (e.g., human, rat, rabbit, sheep, swine, bovine, cat, dog, monkey and the like). Examples of the parenteral administration route include intravenous, intraarterial, intramuscular, intraperitoneal and intratracheal routes and the like.

The dose of the agent containing HB-EGF for protecting the liver/promoting liver regeneration varies depending on the molecular weight of the active ingredient, administration route, severity of disease, animal species to be the subject of administration, drug acceptability, body weight, age and the like of the subject of administration; generally, the dose is within the range of about 0.05 to about 10 mg/kg, preferably about 0.1 to about 5 mg/kg, as the amount of the active ingredient, per day for an adult, which may be administered at once or in several portions.

(2) Agent Containing Nucleic Acid Encoding HB-EGF for Protecting the Liver/Promoting Liver Regeneration The nucleic acid encoding HB-EGF can produce HB-EGF for a long period due to prolonged gene expression and, therefore, is expected to exhibit a sustained treatment effect. Therefore, the nucleic acid can also be preferably used, in addition to the prophylactic or therapeutic effect on acute liver diseases, as an agent for the prophylaxis/inhibition of progression, which is used for preventing exhaustion of hepatocytes and cell death associated with chronic diseases such as chronic hepatitis, liver fibrosis and cirrhosis.

The nucleic acid encoding HB-EGF is preferably administered in the form wherein it is carried on a suitable expression vector. The expression vector is configured at the position where the nucleic acid encoding HB-EGF is functionally linked to a promoter capable of exhibiting promoter activity in a target cell of a mammal, which is the subject of administration, or can be turned into a functionally-linked form in a target cell of the animal administered under given conditions. The promoter to be used is not particularly limited as long as it can function in a target cell of a mammal, which is the subject of administration. Examples of the promoter include virus promoters such as promoters derived from cytomegalovirus (CMV) (e.g., CMV immediate-early promoter), promoters derived from human immunodeficiency virus (HIV) (e.g., HIV LTR), promoters derived from Rous sarcoma virus (RSV) (e.g., RSV LTR), promoters derived from mouse mammary tumor virus (MMTV) (e.g., MMTV LTR), promoters derived from Moloney mouse leukemia virus (MOMLV) (e.g., MoMLV LTR), promoters derived from herpes simplex virus (HSV) (e.g., HSV thymidine kinase (TK) promoter), promoters derived from SV40 (e.g., SV40 early promoter), promoters derived from Epstein-Barr virus (EBV), promoters derived from adeno-associated virus (AAV) (e.g., AAV p5 promoter), and promoters derived from adenovirus (AdV) (Ad2 or Ad5 major late promoter), and constitutive protein gene promoters in mammal such as β-actin gene promoter, PGK gene promoter, transferrin gene promoter, and the like. "Being configured at the position where the expression vector can be turned into a functionally-linked form under a constant condition" means, for example, that as further described below, the expression vector has a structure where the promoter and the nucleic acid encoding HB-EGF are divided by two recombinase recognition sequences configured at the same direction, wherein the two recombinase recognition sequences are separated by a spacer sequence that has a sufficient length to prevent the expression of the nucleic acid from the promoter, the spacer sequence is cleaved out in the presence of a recombinase that specifically recognizes the recognition sequence, and the nucleic acid encoding HB-EGF is configured so as to be functionally linked to the promoter.

The expression vector preferably contains a transcription termination signal, i.e. terminator region, in the downstream of the nucleic acid encoding HB-EGF. The expression vector can further contain a selection marker gene for selection of transformed cells (genes that offer resistance against pharmaceutical agents such as tetracycline, ampicillin, kanamycin, hygromycin, and phosphinothricin, genes that complement an auxotrophic mutation, and the like). When the expression vector has a spacer sequence sandwiched by recombinase recognition sequences as mentioned above, the selection marker gene can be configured within the spacer sequence.

Although vector used as the expression vector of the present invention is not particularly limited, examples of vectors suitable for administration into a mammal such as human include vectors derived from virus such as vretrovirus, adenovirus, adeno-associated virus, herpesvirus, herpes simplex virus, lentivirus, vaccinia virus, poxvirus, poliovirus, sindbisvirus, and Hemagglutinating Virus of Japan. Adenovirus has advantages that it has extremely high efficiency of gene introduction, permits introduction into a nondividing cell, the integration of the introduced gene into a host chromosome is extremely rare, and the like. Particularly, development of next-generation vector named gutted (gutless) vector, wherein almost full-length of adenovirus genome other than packaging signal (ψ) is substituted by introduced gene, has resolved the problem of immunogenicity in first-generation vectors, and thereby long-term sustainability of introduced gene expression has been realized, which results in further increase of usability of adenovirus in gene therapy. Similarly, since adeno-associated virus has comparatively high efficiency of gene introduction, permits introduction into a nondividing cell including hepatocyte, and it has been known from animal experiments that expression of introduced gene on administration into a living organism persists over a long period, adeno-associated virus is preferred as the viral vector in the present invention.

It is possible that constitutive overexpression of HB-EGF causes a side effect in an animal into which the gene has been introduced. Accordingly, in a preferable embodiment of the present invention, the expression vector is capable of expressing HB-EGF in a time- and/or target cell-specific manner in order to prevent adverse influences due to an overexpression of HB-EGF during the period and/or at a site not in need thereof. As the first embodiment of such vector, vectors containing a nucleic acid encoding HB-EGF functionally linked to a promoter derived from a gene that is specifically expressed in a target cell (in the present invention, the target cell is preferably a hepatocyte, but is not limited as long as the target cell can release soluble HB-EGF to deliver same to the liver) of an animal to be the subject of administration can be mentioned. For example, as the liver specific promoters, serum albumin promoter, cytochrome P-450 promoter, and promoters containing a liver-specific transcription factor (HNF1, HNF3, HNF4, C/EBP, and the like)-binding cis-element, and the like can be mentioned.

As the second embodiment of the time- and tissue-specific expression vector of the present invention, vectors containing a nucleic acid encoding HB-EGF functionally linked to an inducible promoter whose expression is trans-regulated by an exogenous substance can be mentioned. When the inducible promoter used is, for example, metallothionein-1 gene promoter, expression of HB-EGF can be induced at any time in a target cell-specific manner by administering topically to a location of target cell an inducing substance, including heavy-metals such as gold, zinc and cadmium, steroids such as dexamethasone, alkylating agents, chelating agents, cytokines and the like, at intended time.

Another preferable embodiment of the time- and tissue-specific expression vector of the present invention is a vector having a structure wherein a promoter and a nucleic acid encoding HB-EGF are divided by a spacer sequence having a sufficient length to prevent expression of nucleic acid from a promoter, i.e., by two recombinase recognition sequences configured in the same direction. Mere introduction of the vector into a target cell is insufficient for a promoter to direct transcription of nucleic acid encoding HB-EGF. However, when a recombinase specifically recognizing the recognition sequence at a desired timing is topically administered to a target cell, or an expression vector containing a nucleic acid encoding the recombinase is topically administered to allow expression of the recombinase in the target cell, homologous recombination via the recombinase takes place between the recognition sequences, as a result of which the spacer sequence is cleaved out, the nucleic acid encoding HB-EGF is functionally linked to the promoter and a target cell specific expression of HB-EGF occurs at a desired timing.

To prevent recombination by a recombinase endogenous in the subject of administration, the recombinase recognition sequence to be used for the above-mentioned vector is desirably a heterologous recombinase recognition sequence which is not recognized by the endogenous recombinase. Accordingly, the recombinase acting trans on the vector is also desirably a heterologous recombinase. The combination of such heterologous recombinase and the recombinase recognition sequence preferably includes, nonlimitatively, *Escherichia coli* bacteriophage P1-derived Crerecombinase and lox Psequence, or yeast-derived F1precombinase and frtsequence.

As a promoter for the time specific and tissue specific expression vector of the present invention utilizing the interaction between recombinase/recombinase recognition sequences, a virus-derived promoter or a promoter of a constituent protein gene of a mammal is preferably used to ensure expression at a desired timing and site.

The expression vector containing a nucleic acid encoding HB-EGF can be produced by using a conventional genetic engineering technique, cell culturing technique and virus preparation technique [for example, *Current Protocols in Molecular Biology*, F. Ausubel et al. eds. (1994) John Wiley & Sons, Inc.; *Molecular Cloning (A Laboratory Manual)*, 3rd ed. Volumes 1-3, Josseph Sambrook & David W. Russel eds., Cold Spring Harbor Laboratory Press (Cold Spring Harbor, N.Y.) (2001); *Culture of Animal Cells; A Manual of Basic Technique*, R. Freshney eds., 2nd ed. (1987), Wiley-Liss; Frank L. Graham, *Manipulation of adenovirus vector*, Chapter 11. p109-p128; E. J. Murray eds., *Methods in Molecular Biology*, Vol. 7, Gene Transfer and Expression Protocols (1991); Chen, S-H. et al., Combination gene therapy for liver metastases of colon carcinoma in vivo., Proc. Natl. Acad. Sci. USA (1995) 92, 2477-2581, and the like].

When a nonviral vector is used as the expression vector containing a nucleic acid encoding HB-EGF, introduction of the expression vector can be performed by using a polymer carrier such as poly-L-lysine-nucleic acid complex, or by encapsulating the vector in a liposome. The liposome is a capsule composed of phospholipid with a particle size of several tens to several hundreds nm, inside of which vectors such as a plasmid encoding HB-EGF can be encapsulated. Alternatively, vectors can be directly introduced into a target cell by using the particle gun method.

In the use of the vector in which the interaction between a recombinase and a recombinase recognition sequence is utilized, when the recombinase per se is topically administered as a trans-acting substance, for example, the recombinase can be dissolved or suspended in a suitable aseptic vehicle and injected into a target site. On the other hand, when a recombinase-expressing vector is topically administered to a target site as a trans-acting substance, the recombinase-expressing vector is not particularly limited as long as the nucleic acid encoding the recombinase has a expression cassette that is functionally linked to a promoter capable of exhibiting a promoter activity in a target cell of subject of administration. When the promoter used is a constitutive promoter, in order to prevent the expression of the recombinase during the period not in need thereof, the vector administered to a target site is preferably one rarely incorporated into a chromosome of host cell, including, for example, adenovirus. As an alternative approach for allowing the expression of recombinase at an intended time, the use of an inducible promoter such as metallothionein gene promoter can be mentioned. In this case, viral vectors with high integration efficiency such as retrovirus can be used.

Also, the expression vector containing a nucleic acid encoding HB-EGF can be, where necessary, mixed with a pharmacologically acceptable carrier and formulated into various forms of preparation such as injection and the like, and used as the above-mentioned pharmaceutical agent. Here, examples of the pharmacologically acceptable carrier include, but are not limited to, those mentioned above as preparations containing HB-EGF.

An agent containing an expression vector containing a nucleic acid encoding HB-EGF for protecting the liver/promoting liver regeneration is administered by either ex vivo method wherein the target cell of the treatment target animal itself or a cell from an animal (allogeneic or heterologous to the treatment target animal) is extracted out of the body, cultured, subjected to infection, and put back (or transplanted) into the body, or in vivo method wherein the vector is directly administered into the body of the subject of administration to perform introduction. In the case of the ex vivo method, the introduction of the vector into the target cell can be performed by the microinjection method, calcium phosphate coprecipitation method, PEG method, electroporation method and the like. In the case of the in vivo method, the administration of the preparation can be performed by, for example, injection, catheter, balloon catheter and the like.

Dose of the agent for protecting the liver/promoting liver regeneration of the present invention containing the expression vector containing the nucleic acid encoding HB-EGF varies depending on the kind of vector, size of active ingredient molecule, promoter activity, administration route, severity of illness, the animal species to be the subject of administration, drug acceptability, body weight, age and the like of the subject of administration. For example, when adenovirus is used as the viral vector, since the safety was confirmed using $2\times10^{11}$ particles/kg (virus particles) in a clinical test of conventional gene therapy for liver diseases, this amount can be used as a rough standard dose. For example, the dose is about $2\times10^{9}$ to about $2\times10^{11}$ particles/kg, preferably about $2\times10^{10}$ to about $2\times10^{11}$ particles/kg, for an adult per day. Note that when HB-EGF is actually administered, HB-EGF gene does not need to be introduced into all hepatocytes since the liver diseases are not congenital diseases and an amount not more than this level is considered to be sufficient for practical purposes. On the other hand, when a nonviral vector is encapsulated in a liposome, since the safety was confirmed by intravenous administration of 666 µg of DNA in a clinical research using a cynomolgus with a body weight of about 4 kg, this amount can be used as a rough standard dose. For example, the single dose for an adult is about 2 to about 10 mg, preferably about 5 to about 8 mg.

The present invention also intends liver protection and promotion of liver regeneration, and further, prophylaxis/treatment of liver diseases, by potentiating expression of endogenous HB-EGF gene and activity of HB-EGF.

As the means for potentiating the expression of endogenous HB-EGF gene, for example, administration of a transactivation factor, which binds to a regulate region of HB-EGF gene to activate the transcription thereof, a substance that stabilizes HB-EGF mRNA, and a substance that increases translation efficiency from HB-EGF mRNA, and the like can be mentioned; as the means for potentiating the activity of endogenous HB-EGF, for example, administration of a substance that promotes production of active form of soluble HB-EGF from pro-HB-EGF (e.g., specific proteases that are involved in shedding such as ADAM, and the like), a substance that suppresses the decomposition of HB-EGF (e.g., protease inhibitors and the like), and the like can be mentioned.

Accordingly, another aspect of the present invention provides a screening method of substances for protecting the liver/promoting liver regeneration, comprising selecting the above-mentioned substance that enhances the expression of endogenous HB-EGF gene and the activity of HB-EGF. The screening method is characterized by culturing a cell that expresses HB-EGF by nature in the presence of and in the absence of a test substance, and comparing expression amount and/or activity of HB-EGF. The expression amount of HB-EGF can be examined at transcriptional level by using Northern blot or RT-PCR, or at translational level by immunoassay using an anti-HB-EGF antibody and the like. On the other hand, the activity of HB-EGF can be examined by investigating the growth-stimulating activity in a cell such as hepatocyte, or by using activation of EGFR family (phosphorylation of the receptor, and the like), which is a target receptor of HB-EGF, or activation of a kinase molecule such as MAPK, which is activated at the downstream of EGFR family, as an index.

The thus selected substance mentioned above, which is capable of enhancing expression of endogenous HB-EGF gene and activity of HB-EGF, can be prepared, for example, as a pharmaceutical composition along with a pharmacologically acceptable carrier in the same manner as mentioned above for the agent containing HB-EGF for protecting the liver/promoting liver regeneration, and administered orally or parenterally to a mammal such as human as an agent for protecting the liver/promoting liver regeneration.

Dose of the agent containing the substance for protecting the liver/promoting liver regeneration varies depending on kind and molecular weight of active ingredient, administration route, severity of illness, the animal species to be the subject of administration, drug acceptability, body weight, age and the like of the subject of administration; generally, the dose is within the range of about 0.001 to about 100 mg/kg, preferably about 1 to about 10 mg/kg, as the amount of an active ingredient, per day for an adult, which can be administered at once or in several portions.

Abbreviations for bases, amino acids and the like used herein are based on abbreviations specified by the IUPAC-IUB Commission on Biochemical Nomenclature or abbreviations in common use in relevant fields. Some examples are given below. When an enantiomer may be present in amino acid, it is of the L-configuration, unless otherwise stated.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
pGlu: Pyroglutamic acid
Me: Methyl group
Et: Ethyl group
Bu: Butyl group
Ph: Phenyl group
TC: Thiazolidine-4(R)-carboxamide group Substituents, protecting groups and reagents frequently mentioned herein are represented by the symbols shown below.

Tos: p-Toluenesulfonyl
CHO: Formyl
Bzl: Benzyl

Cl$_2$Bzl: 2,6-Dichlorobenzyl
Bom: Benzyloxymethyl
Z: Benzyloxycarbonyl
Cl—Z: 2-Chlorobenzyloxycarbonyl
Br—Z: 2-Bromobenzyloxycarbonyl
Boc: t-Butoxycarbonyl
DNP: Dinitrophenol
Trt: Trityl
Bum: t-Butoxymethyl
Fmoc: N-9-Fluorenylmethoxycarbonyl
HOBt: 1-Hydroxybenztriazole
HOOBt: 3,4-Dihydro-3-hydroxy-4-oxo-1,2,3-benzotriazine
HONB: 1-Hydroxy-5-norbornene-2,3-dicarboximide
DCC: N,N'-Dicyclohexylcarbodiimide The present invention is explained in more detail in the following by referring to examples, which are mere examples and do not limit the scope of the present invention in any way. In the examples, genetic engineering techniques and cell culturing techniques handling plasmids, DNA, various enzymes, *Escherichia coli*, cultured cells and the like were performed according to the methods described in the above-mentioned *Current Protocols in Molecular Biology*, F. Ausubel et al. eds. (1994) John Wiley & Sons, Inc.; *Molecular Cloning (A Laboratory Manual)*, 3rd ed. Volume 1-3, Josseph Sambrook & David W. Russel eds., Cold Spring Harbor Laboratory Press (Cold Spring Harbor, N.Y.) (2001); *Culture of Animal Cells; A Manual of Basic Technique*, R. Freshney eds., 2nd ed. (1987) Wiley-Liss, unless otherwise stated. Unless otherwise stated, general handling of adenovirus was performed according to the methods described in the above-mentioned Frank L. Graham, *Manipulation of adenovirus vector*, Chapter 11, p109-p128; E. J. Murray eds., *Methods in Molecular Biology*, Vol. 7: Gene Transfer and Expression Protocols (1991); Chen, S-H. et al., Combination gene therapy for liver metastases of colon carcinoma in vivo., *Proc. Natl. Acad. Sci. USA* (1995) 92, 2477-2581. Regarding therapeutic effects and phenomena, a significant difference among any groups was first analyzed by Anova test, and subsequently an individual significant difference between each two group was analyzed by Student t-test (asymmetric two-group t-test). A significant difference in survival rate was analyzed using Kaplan-Meier test.

EXAMPLES

Example 1

Construction of Adenoviral Vector

Adenoviral vectors used in Experimental Examples described below were produced as the following.

Plasmid pADL.1/RSV (B. Fang et al., Gene Therapy (1994) 1, 247-254) was a plasmid produced by incorporating, from upstream, a 0-455 base portion from 3' side of human adenovirus type 5, Rous sarcoma virus (RSV) LTR promoter, multicloning site, poly A signal sequence of bovine growth hormone, and a 3328-5788 base portion from 3' side of human adenovirus type 5 into pBR322 plasmid, and offered from Shu-Hsia Chen (Mount Sinai University). The pADL.1/RSV plasmid was digested with restriction enzymes Hind III and Not I and purified to give a vector to be used for ligation. On the other hand, plasmid pRcHBEGF, containing cDNA of the full length of ORF of human HB-EGF in plasmid pRc/CMV (Invitrogen), was offered from Eisuke Mekada (Research Institute for Microbial Diseases, Osaka University). The pRcHBEGF plasmid was digested with restriction enzymes Hind III and Not I to excise the full length of HB-EGF cDNA, which was subjected to agarose gel electrophoresis, and the intended DNA fragment was recovered from the gel and purified to give an insert to be used for ligation. The thus treated pADL.1/RSV vector and HB-EGF cDNA insert were subjected to a ligation-reaction using T4 DNA ligase to obtain pADL.1/RSV-HB-EGF. Furthermore, the pADL.1/RSV-HB-EGF was, together with plasmid pJM17 (Micorobix Biosystems Inc.) containing a gene other than E1 region of human adenovirus type 5, co-transfected into 293 cell by calcium phosphate method. This caused a plaque containing the correct intended adenovirus to emerge by homologous recombination 10 to 14 days after the co-transfection. This plaque was picked up, and the correct non-proliferating recombinant adenovirus Ad.HB-EGF expressing the intended HB-EGF was confirmed by immunostaining using an anti-HB-EGF antibody (M-18:sc-1414, SANTA CRUZ), and the like, after which the Ad.HB-EGF was proliferated by 293 cell, and concentrated by density gradient centrifugation in cesium chloride. The concentrated virus was purified with an Econo-Pac 10DG desalting column (Bio-Rad Cat. No. 732-2011), eluted with PBS(-), added with glycerol, frozen in liquid nitrogen, and preserved at –80° C. When the virus was used, the particle volume was calculated, the solution was diluted with PBS(-) so as to achieve an administered volume of 100 μl/animal, and the diluted solution was administered.

A recombinant adenovirus AD.LacZ expressing LacZ gene of *Escherichia coli* used for confirmation of gene introduction was produced by the same method as described above; details of the Ad.LacZ production method are described in *Proc. Natl. Acad. Sci. USA* (1995) 92, 2577-2581. HB-EGF is not incorporated into Ad.dE1.3, which is, therefore, a recombinant adenovirus not expressing these genes at all. Ad.dE1.3 was produced by co-transfecting pADL1/RSV not inserted by HB-EGF and pJM17 into 293 cell as mentioned above and following the same method and the process. Human HB-EGF cDNA is described in Higashiyama, S. et al., *Science* 251: 936-939 (1991), and Gene Bank accession number thereof is M60278 (the same sequence as NM_001945).

Experimental Example 1 Confirmation of Gene Introduction into Liver by Adenoviral Vector Adenoviral vector Ad.LacZ and Ad.HB-EGF ($1\times10^{11}$ particles) prepared in Example 1 were injected into 6-week-old male C57BL/6J mice (CHUBU SCIENCE Co., Ltd.; 10 animals per group) from the tail vein, and the expressions of exogenous LacZ and HB-EGF in the liver were examined by X-gal staining and immunostaining, respectively. The mice were given general anesthesia with ether, and their chest was opened, and their organs (heart, lung, liver, kidney, spleen) were collected. After the collection, the organs were equally divided into two; one was used for preparing an OCT specimen with a compound (TissueTek OCT compound), and another was, after fixation with 10% formaldehyde, used for preparing a paraffin-embedded specimen. X-gal staining was performed by fixing OCT specimen section with 0.2% formaldehyde/0.02% glutaraldehyde fixative for 30 min, followed by immersion in X-gal staining solution and a reaction at 37° C. for 24 hr. To perform immunostaining, the paraffin-embedded specimen was fixed with 4% para-formaldehyde for 10 min, blocked with 10% skim milk (Snow Brand Milk Products Co., Ltd.) for 60 min; subsequently, reacted with a primary antibody (anti-human HB-EGF goat polyclonal antibody, R&D Systems Inc., Minneapolis, Minn. Cat. No. AF-259-NA) 100-fold diluted solution (2 µg/ml) for 1 hr, and visualization of HB-EGF was performed by labeling same with anti-goat Alexa568 (MOLECULAR PROBES, Inc., Eugene, Oreg. Cat. No. A-11029). Nuclear staining was performed with a 1000-fold diluted Hoechst33342 (MOLECULAR PROBES, Inc., Eugene, Oreg. Cat. No. H-3570) for 5 min. Recording of observed images was performed with a confocal laser microscope (Carl Zeiss product number LSM510). Results of X-gal staining and immunostaining are shown in FIG. 1 with a sample which was injected with Ad.dE1.3 from the tail vein and treated in the same manner being an unstained negative control.

Figure 1B:
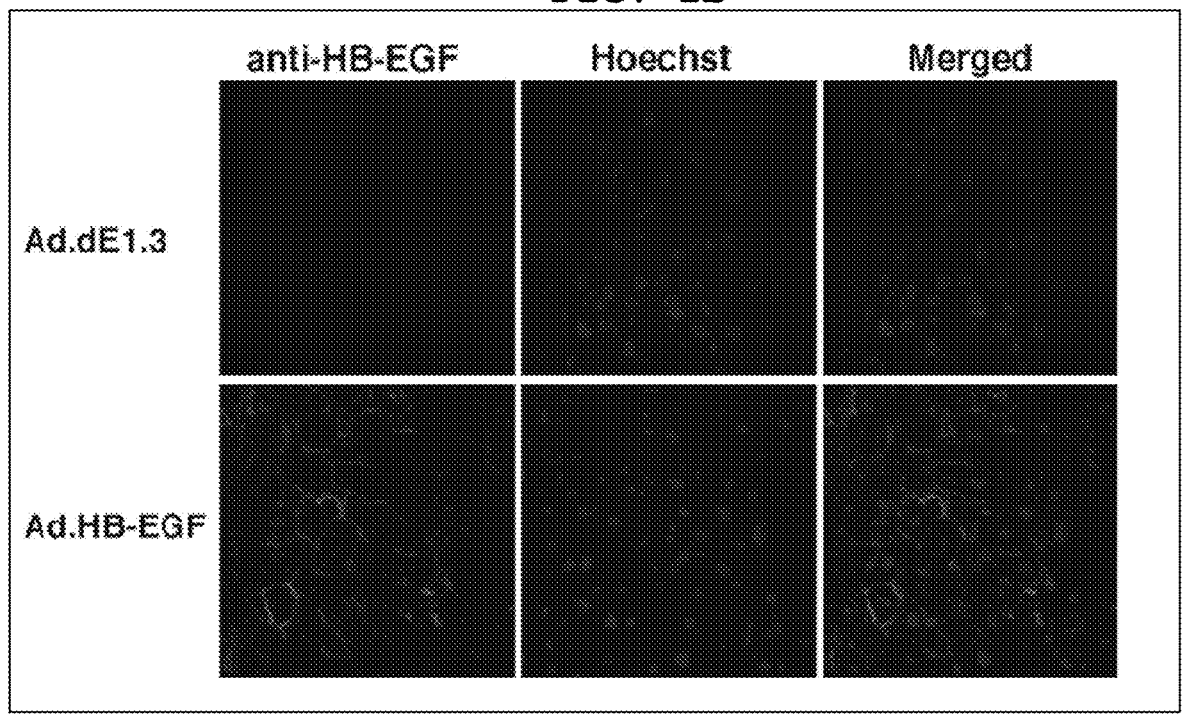
FIG. 1B shows that HB-EGF expression is observed at the edge of the cellular membrane by introducing Ad.HB-EGF.

As FIG. 1 shows, since X-gal staining was observed in 60 to 90% of hepatocytes from livers of mice which had been injected with Ad.LacZ from the tail vein, it was demonstrated that tail vein injection of adenoviral vector enabled efficient gene introduction into a hepatocyte (FIG. 1A). Furthermore, in mouse livers into which Ad.HB-EGF was injected from the tail vein, mainly expression of HB-EGF in cellular membrane was observed and, hence, it was demonstrated that an exogeneous HB-EGF with biological activity was synthesized as a membrane-binding type HB-EGF, or a further processed soluble HB-EGF acted on a hepatocyte in an autocrine manner (FIG. 1B).

Figure 2A:
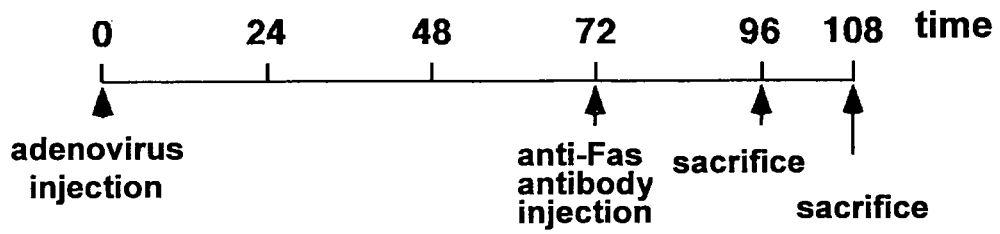
FIG. 2A shows the schedule of the experiment.

Experimental Example 2 Inhibitory Effect of Elevation in Blood Concentration of Liver Enzyme by Ad.HB-EGF 6-week-old male C57BL/6J mice (CHUBU SCIENCE Co., Ltd.; 10 animals/group) were injected with a Fas agonist antibody (anti-mouse Fas mouse monoclonal antibody, clone name, Jo-2, Becktone-Dickinson Bioscience, San Jose, Calif. Cat. No. 554255) from the tail vein at 4 µg per animal to prepare a Fas-induced fulminant hepatic failure model. To investigate the effect of prevention and treatment of fulminant hepatic failure, the adenoviral vectors (Ad.HB-EGF, Ad.HGF, Ad.LacZ, and Ad.dE1.3) were previously injected from the tail vein at $1 \times 10^{11}$ particles per animal 72 hr before the injection of the Fas agonist antibody from the tail vein. Blood samples were collected at 24 hr and 36 hr after the tail vein injection of the Fas agonist antibody (96 hr and 108 hr after the tail vein injection of adenovirus, respectively), the mouse were sacrificed, and the organs were collected (the experimental schedule is shown in FIG. 2A). Liver function, which is an index of prevention of onset and treatment of fulminant hepatic failure, was evaluated by measuring alanine aminotransferase (ALT) and aspartic acid aminotransferase (AST), which are liver enzymes in liver. The measurement was carried out using an automatic clinical analyzer Hitachi 736 (Hitachi, Ltd.) according to a conventional method.

Figure 2B:
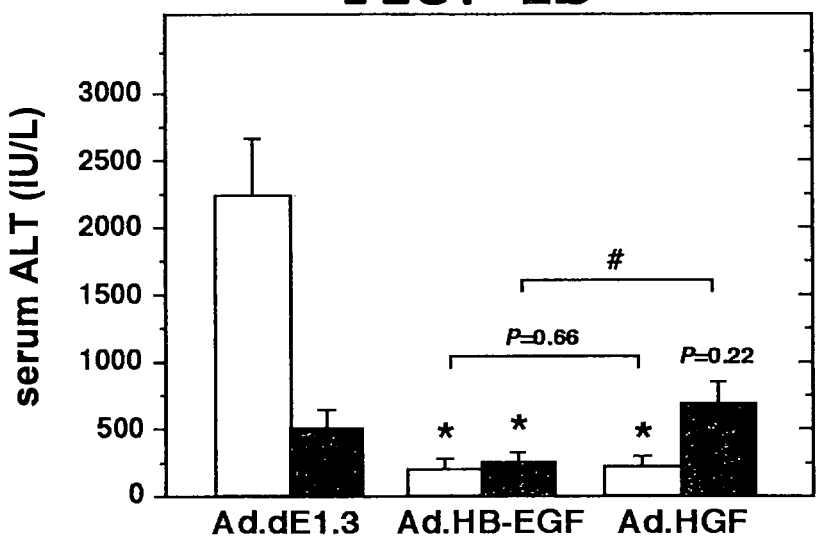
FIG. 2B shows the serum ALT value and FIG. 2C shows the serum AST value (white bar: 24 hr after antibody administration, black bar: 36 hr after antibody administration).
Figure 2C:
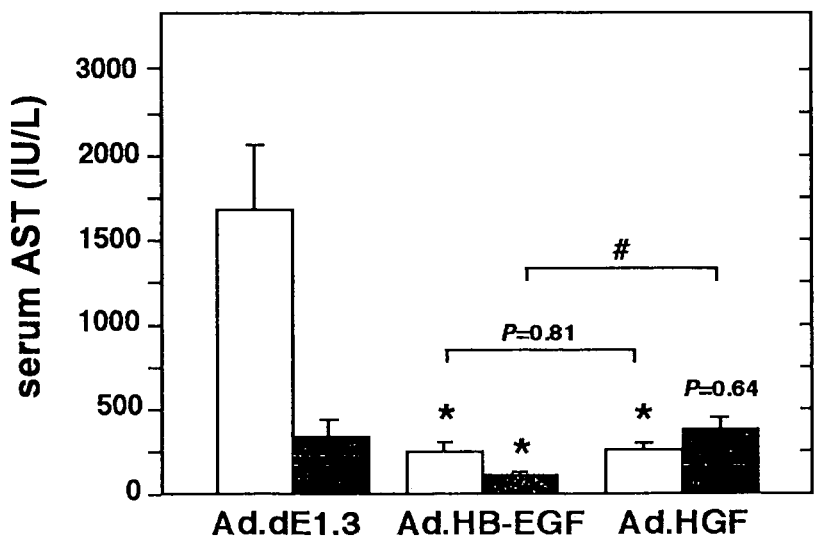

As shown in FIGS. 2B and 2C, the results of measuring the serum ALT and AST level after the blood sampling demonstrated that at 24 hr after the tail vein injection of the agonist Fas antibody, while the levels of ALT and AST were elevated to 2240±450 and 1665±391 IU/L, respectively, in the Ad.dE1.3-administered group, both the levels were not more than 230 IU/L in the Ad.HB-EGF-administered group, showing inhibition of elevation in ALT and AST level. Furthermore, it was demonstrated that in this inhibitory effect of elevation in liver enzyme in blood, HB-EGF showed the equivalent effect to HGF, only which had been known to show strong effect of prevention and treatment of fulminant hepatic failure. It was also demonstrated that at 36 hr after administration of antibody, ALT and AST level were decreased to not more than 500 IU/L even in the Ad.dE1.3-administered group; while in the Ad.HGF-administered group, there observed no significant difference with this, in the Ad.HB-EGF-administered group, the levels were not more than 250 IU/L, which were significantly lower than that in the Ad.dE1.3-administered group. From the above results, it was demonstrated that Ad.HB-EGF inhibited and relieved liver damage associated with fulminant hepatic failure, and the effect was more potent than that of Ad.HGF.

Experimental Example 3 Inhibitory Effect of Hepatocyte Apoptosis by Ad.HB-EGF

Hepatocyte death due to apoptosis, which is a main pathology of fulminant hepatic failure, was evaluated by performing HE staining and TUNEL staining of liver tissues. Sections were respectively prepared from the paraffin-embedded specimen and OCT specimen of mouse livers at 24 hr and 36 hr after the agonist antibody administration (96 hr and 108 hr after the tail vein injection of adenovirus, respectively), and subjected to HE staining and TUNEL staining.

Figure 3:
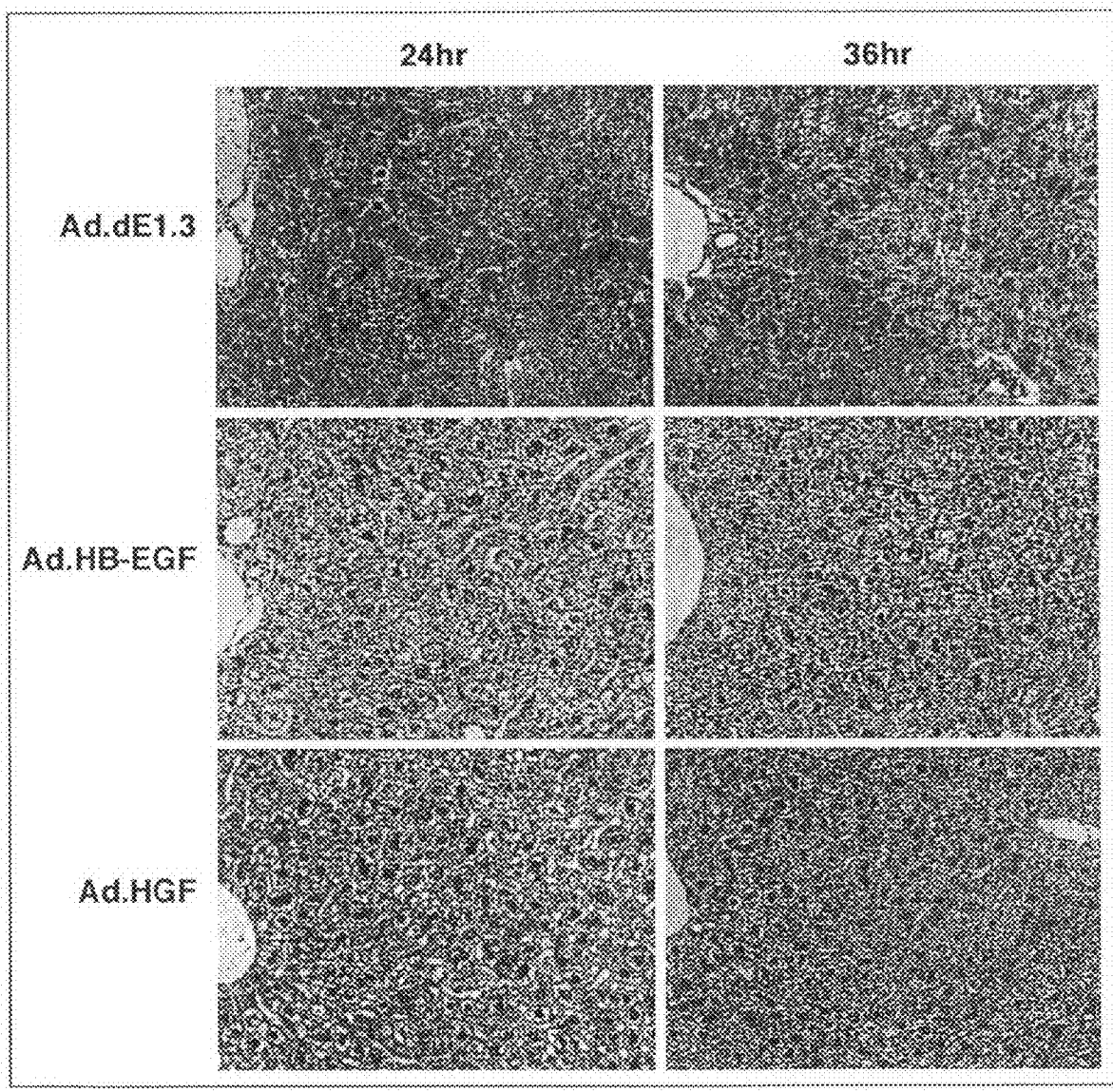
FIG. 3 shows an influence of the administration of Ad.HB-EGF (middle), Ad.HGF (bottom) or Ad.dE1.3 (top) on liver tissue apoptosis in fulminant hepatic failure model mice. The left side and right side images are microscopic images of liver tissues of each administration group mouse 24 hr after administration and 36 hr after administration, respectively.
Figure 4A:
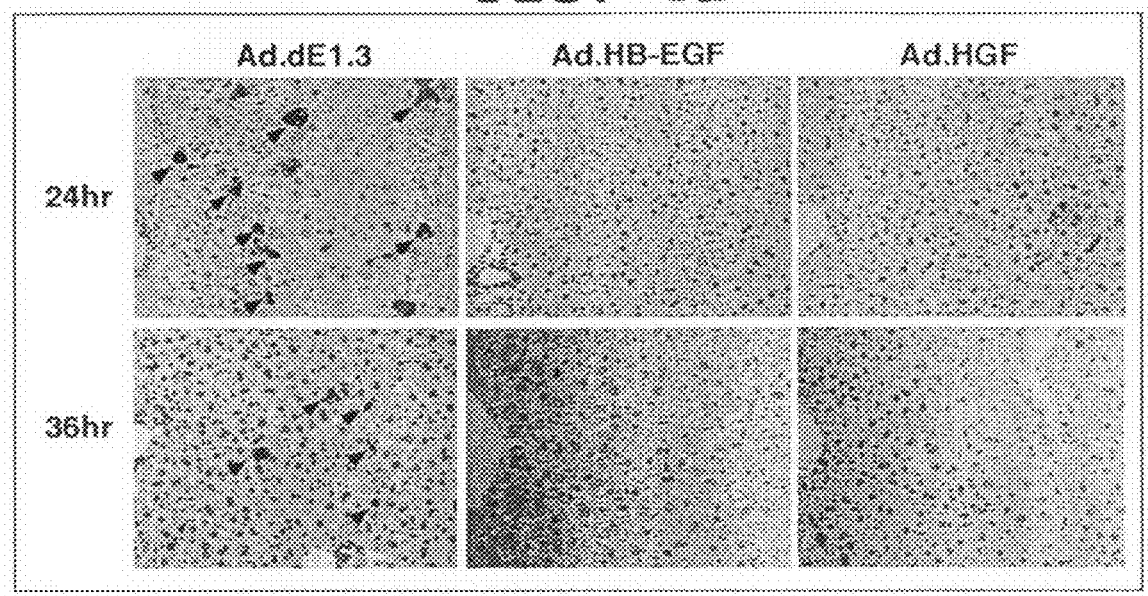
FIG. 4A shows, from the left, microscopic images of the Ad.dE1.3-, Ad.HB-EGF-, or Ad.HGF-administration group mice (top: 24 hr after antibody administration, bottom: 36 hr after antibody administration).
Figure 4B:
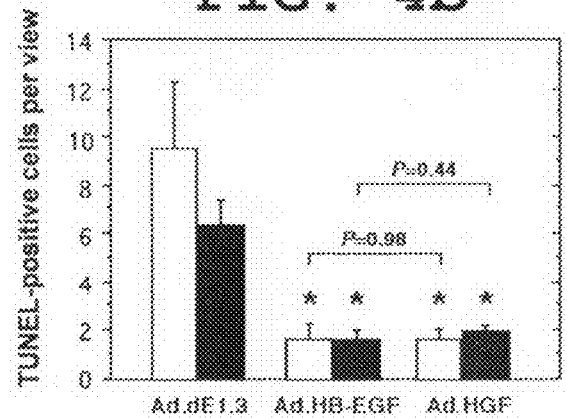
FIG. 4B is a graph showing quantified TUNEL-positive cells (white bar: 24 hr after antibody administration, black bar: 36 hr after antibody administration).

As shown in FIG. 3, while in the Ad.dE1.3-administered group, hepatocytes exhibiting typical apoptotic morphology accompanying infiltration of neutrophils and macrophages, corresponding to the elevation in the level of liver enzyme (FIGS. 2B and 2C), were observed at 24 hr later, in the Ad.HB-EGF-administered group, as well as in the Ad.HGF-administered group, apoptotic morphology of hepatocytes was not observed. Furthermore, at 36 hr later, while in the Ad.dE1.3-administered group, dropout of liver tissue due to progression of hepatocellular apoptosis was observed, and also in the Ad.HGF-administered group inflammation was observed, in the Ad.HB-EGF, disorder of liver tissue was almost completely inhibited.

Furthermore, TUNEL staining was performed in order to evaluate hepatocellular apoptosis in detail; as a result, both at 24 hr and 36 hr later, compared to the number of TUNEL-positive hepatocytes in the Ad.dE1.3-administered group, the positive cell number was significantly smaller in the Ad.HB-EGF-administered group and Ad.HGF group, thereby it was demonstrated that in Ad.HB-EGF- and Ad.HGF-administered group, hepatocellular apoptosis, which is an essence of fulminant hepatic failure, was inhibited.

Experimental Example 4 Promoting Effect of Liver Regeneration by Ad.HB-EGF

Liver regeneration, which is an index of essential therapeutic effect of fulminant hepatic failure, was evaluated with the ratio of proliferating hepatocytes identified by anti-Ki-67 mouse monoclonal antibody (clone name, TEC-3, Dako Cytomation, Denmark). Immunostaining with anti-Ki-67 antibody was performed using paraffin sections of mouse liver at 24 hr and 36 hr after the agonist antibody administration (96 hr and 108 hr after the tail vein injection of adenovirus, respectively).

As shown in FIG. 5, while in the Ad.dE1.3-administered group, Ki-67-positive cells, which signifies the growth of hepatocyte, were hardly detected both at 24 and 36 hr later, in the Ad.HB-EGF-administered group, as well as in the Ad.HGF group, significant increase in Ki-67-positive cell was observed. Particularly, the ratio of Ki-67-positive cell at 24 hr later in the Ad.HB-EGF-administered group was about 1.5-fold higher compared to HGF, only which has been reported as a potent therapeutic factor for fulminant hepatic failure, thereby it was demonstrated that HB-EGF had therapeutic effect for fulminant hepatic failure surpassing HGF.

These results suggest that HB-EGF, which is expressed in liver after administration of the Ad.HB-EGF, be effective in preventing onset and progression of the pathology by strongly inhibiting hepatocellular apoptosis, which is an essence of fulminant hepatic failure, and in inducing an essential healing by promoting liver regeneration, specifically proliferation of surviving hepatocytes. Accordingly, the pharmaceutical agent of the present invention using HB-EGF can be also applied to any other diseases accompanying liver damage (hepatocyte death).

INDUSTRIAL APPLICABILITY

HB-EGF exhibits strong actions of inhibiting liver damage and apoptosis and inducing liver regeneration; therefore, HB-EGF or nucleic acids encoding same are extremely useful as a drug for prevention and treatment of various diseases accompanying liver damage or hepatocyte death, particularly liver diseases such as fulminant hepatic failure.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

This application is based on patent application No. 2005-283085 filed in Japan, and the contents disclosed therein are hereby entirely incorporated by reference. In addition, the contents disclosed in any publication cited herein, including patents and patent applications, are hereby incorporated in their entireties by reference, to the extent that they have been disclosed herein.

The invention claimed is:

1. A method for inhibiting hepatocellular apoptosis and promoting proliferation of surviving hepatocytes in a mammal with Fas-mediated liver damage, comprising intravenously or intramuscularly administering to said mammal an effective amount of a vector carrying a nucleic acid encoding a heparin-binding EGF-like growth factor (HB-EGF), wherein the administration of the vector results in the expression of the HB-EGF in hepatocytes in said mammal, thereby inhibiting hepatocellular apoptosis and promoting proliferation of surviving hepatocytes.

2. The method of claim 1, wherein the nucleic acid is carried on a viral vector.

3. The method of claim 2, wherein the viral vector is selected from the group consisting of adenoviral vector, adeno-associated viral vector, retroviral vector, lentiviral vector and herpes viral vector.

4. The method of claim 1, wherein the vector is administered by an injection.

5. The method of claim 4, wherein the injection is an intravenous injection or intramuscular injection.

6. The method of claim 4, wherein the injection is an intravenous injection.

7. The method of claim 6, wherein the nucleic acid is carried on an adenoviral vector and the vector is administered in an amount capable of introducing the nucleic acid into 60% or more of total hepatocytes.

8. The method of claim 7, wherein the nucleic acid is administered by an injection, a catheter or a balloon catheter.

9. The method of claim 1, wherein the mammal suffers from a Fas-mediated liver disease which is selected from the group consisting of fulminant hepatic failure and acute hepatitis.

10. The method of claim 9, wherein the nucleic acid is administered by an intravenous injection or intramuscular injection.

\* \* \* \* \*